(12) United States Patent
Fukumoto

(10) Patent No.: US 11,192,851 B2
(45) Date of Patent: Dec. 7, 2021

(54) CRYSTAL OF L-ALANYL-L-GLUTAMINE AND METHOD FOR PRODUCING SAME

(71) Applicant: KYOWA HAKKO BIO CO., LTD., Tokyo (JP)

(72) Inventor: Kazunari Fukumoto, Tokyo (JP)

(73) Assignee: KYOWA HAKKO BIO CO., LTD., Tokyo (JP)

(*) Notice: Subject to any disclaimer, the term of this patent is extended or adjusted under 35 U.S.C. 154(b) by 232 days.

(21) Appl. No.: 16/471,557

(22) PCT Filed: Dec. 20, 2017

(86) PCT No.: PCT/JP2017/045666
§ 371 (c)(1),
(2) Date: Jun. 19, 2019

(87) PCT Pub. No.: WO2018/117140
PCT Pub. Date: Jun. 28, 2018

(65) Prior Publication Data
US 2019/0382337 A1   Dec. 19, 2019

(30) Foreign Application Priority Data
Dec. 20, 2016  (JP) .............................. JP2016-246116

(51) Int. Cl.
| | | |
|---|---|---|
| C07C 237/04 | (2006.01) | |
| C07C 231/24 | (2006.01) | |
| C30B 29/58 | (2006.01) | |
| G01N 23/20008 | (2018.01) | |
| G01N 23/207 | (2018.01) | |

(52) U.S. Cl.
CPC .......... *C07C 237/04* (2013.01); *C07C 231/24* (2013.01); *C30B 29/58* (2013.01); *G01N 23/207* (2013.01); *G01N 23/20008* (2013.01)

(58) Field of Classification Search
CPC .............................. C07C 237/04; C07C 231/24
See application file for complete search history.

(56) References Cited

U.S. PATENT DOCUMENTS

| | | | |
|---|---|---|---|
| 5,380,934 A | 1/1995 | Inoue et al. | |
| 5,550,283 A | 8/1996 | Inoue et al. | |
| 5,621,137 A * | 4/1997 | Naruse | A23G 3/346 560/41 |
| 8,685,914 B2* | 4/2014 | Hashimoto | C12P 13/06 514/1.1 |
| 2005/0233977 A1 | 10/2005 | Zhao et al. | |
| 2009/0130708 A1 | 5/2009 | Hashimoto et al. | |

FOREIGN PATENT DOCUMENTS

| | | |
|---|---|---|
| CN | 101519428 A | 9/2009 |
| CN | 103073617 A | 5/2013 |
| CN | 103387600 A | 11/2013 |
| CN | 103588860 A | 2/2014 |
| CN | 103626839 A | 3/2014 |
| CN | 105085612 A | 11/2015 |
| CN | 105237617 A | 1/2016 |
| JP | H06-234715 A | 8/1994 |
| JP | 2005-538963 A | 12/2005 |
| JP | 2010-260853 A | 11/2010 |
| WO | 2006/104186 A1 | 10/2006 |

OTHER PUBLICATIONS

European Patent Office, Extended European Search Report in European Patent Application No. 17885114.3 (dated Jul. 3, 2020).
Akabori et al., "Protection of Amide-Nitrogen for Peptide Synthesis. A Novel Synthesis of Peptides Containing C-Terminal Glutamine," *Bulletin of Chemical Society of Japan*, 34: 739 (1961).
Shimonishi et al., "Studies on the Synthesis of Peptides Containing Glutamine as the C-Terminal. I. Protection of Amide-nitrogen with Xanthyl Group during Peptide Synthesis," *Bulletin of Chemical Society of Japan*, 35(12): 1966-1970 (1962).
Japanese Patent Office, International Search Report in International Patent Application No. PCT/JP2017/045666 (dated Mar. 27, 2018).
Japanese Patent Office, Notice of Reasons for Refusal in Japanese Patent Application No. 2018-558025 (dated Oct. 22, 2021).

* cited by examiner

*Primary Examiner* — Matthew P Coughlin
(74) *Attorney, Agent, or Firm* — Leydig, Voit & Mayer, Ltd.

(57) ABSTRACT

An object of the present invention is to provide a crystal of L-alanyl-L-glutamine having a low loose specific volume, and a method for producing the same. The present invention relates to a crystal of L-alanyl-L-glutamine in which the loose specific volume is 5.0 mL/g or less, and a method for producing the same.

18 Claims, 10 Drawing Sheets

CRYSTAL OF L-ALANYL-L-GLUTAMINE AND METHOD FOR PRODUCING SAME

CROSS-REFERENCE TO RELATED APPLICATIONS

This patent application is the U.S. national phase of International Patent Application No. PCT/JP2017/045666, filed Dec. 20, 2017, which claims the benefit of Japanese Patent Application No. 2016-246116, filed on Dec. 20, 2016, which are incorporated by reference in their entireties herein.

TECHNICAL FIELD

The present invention relates to a crystal of L-alanyl-L-glutamine, which is useful, for example, as a product, a raw material, an intermediate, or the like of health food, pharmaceuticals, cosmetics, and the like, and a method for producing the same.

BACKGROUND ART

L-alanyl-L-glutamine is a dipeptide consisting of L-alanine and L-glutamine, and is known to be used as an energy source for cell division, to have an effect of promoting wound healing, and the like, similar to L-glutamine. On the other hand, because the stability and the solubility in water of are significantly improved as compared to L-glutamine, it has been widely used as pharmaceutical raw materials such as components of infusion, cosmetics, or components of a serum-free medium.

As a crystal of L-alanyl-L-glutamine, a crystal of nonhydrate (Patent Document 1) and monohydrate (Patent Document 2, and Non-Patent Documents 1 and 2) have been known. These crystals, for example, are produced by crystallization by means of adding a solvent to an aqueous solution of L-alanyl-L-glutamine obtained by a fermentation method, an enzyme method, a chemical synthesis method, or the like.

RELATED ART

Patent Document

Patent Document 1: Japanese Patent No. 4931801
Patent Document 2: JP-A-S36-11475

Non-Patent Document

Non-Patent Document 1: Bulletin of the Chemical Society of Japan (1961), 34, p 739
Non-Patent Document 2: Bulletin of the Chemical Society of Japan (1962), 35, p 1966-1970

DISCLOSURE OF INVENTION

Problems to be Solved by the Invention

However, the crystal growth rate of L-alanyl-L-glutamine is very slow in the production methods described in Patent Documents 1 and 2 and Non-patent Documents 1 and 2, and thus, it is difficult to enlarge the crystals, and the obtained crystals are all needle crystals. As a result, there arises a problem that the crystals obtained by those production methods have a high specific volume and a large angle of repose, a low filling ratio to a container, and a poor tableting property.

Therefore, an object of the present invention is to provide a crystal of L-alanyl-L-glutamine having a low loose specific volume, and a method for producing the same.

Means for Solving the Problems

The present invention relates to the following [1] to [17].
(1) A crystal of L-alanyl-L-glutamine, in which the loose specific volume is 5.0 mL/g or less.
(2) The crystal described in (1) above, in which the angle of repose is 50° or less.
(3) The crystal described in (1) or (2) above, which is a crystal of L-alanyl-L-glutamine nonhydrate.
(4) The crystal described in (3) above, which has peaks at diffraction angles ($2\theta°$) of 13.7°±0.2°, preferably ±0.1°, 20.7°±0.2°, preferably ±0.1°, and 34.9°±0.2°, preferably ±0.1° in powder X-ray diffraction.
(5) The crystal described in (4) above, which further has peaks at diffraction angles ($2\theta°$) of 21.5°±0.2°, preferably ±0.1°, and 22.3°±0.2°, preferably ±0.1° in powder X-ray diffraction.
(6) The crystal described in (1) or (2) above, which is a crystal of L-alanyl-L-glutamine n-ethanolate (wherein, n represents any number greater than 0, preferably any number greater than 0 and equal to or smaller than 5, more preferably any number greater than 0 and equal to or smaller than 3, still more preferably any number greater than 0 and equal to or smaller than 1, particularly preferably any number rounded up to the first decimal place that is greater than 0 and equal to or smaller than 1, and most preferably any number rounded up to the second decimal place that is greater than 0 and equal to or smaller than 1).
(7) The crystal described in (6) above, which has peaks at diffraction angles ($2\theta°$) of 10.7°±0.2°, preferably ±0.1°, 20.7°±0.2°, preferably ±0.1°, 21.4°±0.2°, preferably ±0.1°, 23.3°±0.2°, preferably ±0.1°, and 34.8°±0.2°, preferably ±0.1° in powder X-ray diffraction.
(8) The crystal described in (7) above, which further has peaks at diffraction angles ($2\theta°$) of 18.4°±0.2°, preferably ±0.1°, 24.7°±0.2°, preferably ±0.1°, 27.9°±0.2°, preferably ±0.1°, and 32.3°±0.2°, preferably ±0.1° in powder X-ray diffraction.
(9) The crystal described in (1) or (2) above, which is a crystal of L-alanyl-L-glutamine dihydrate.
(10) The crystal described in (9) above, which has peaks at diffraction angles ($2\theta°$) of 11.6°±0.2°, preferably ±0.1°, 23.3°±0.2°, preferably ±0.1°, 23.9°±0.2°, preferably ±0.1°, 27.9°±0.2°, preferably ±0.1°, and 35.3°±0.2°, preferably ±0.1° in powder X-ray diffraction.
(11) The crystal described in (10) above, which further has peaks at diffraction angles ($2\theta°$) of 7.9°±0.2°, preferably ±0.1°, 12.8°±0.2°, preferably ±0.1°, 18.3°±0.2°, preferably ±0.1°, 21.6°±0.2°, preferably ±0.1°, and 24.7°±0.2°, preferably ±0.1° in powder X-ray diffraction.
(12) A method for producing the crystal according to any one of (3) to (5) above, which includes the following steps (1a) to (1c) (wherein, the definition of n is the same as (6) above):
(1a) the step of precipitating a crystal of L-alanyl-L-glutamine n-ethanolate by adding or dropping ethanol to an aqueous solution in which L-alanyl-L-glutamine is dissolved, or the step of transforming the crystal of L-alanyl-L-glutamine nonhydrate to a crystal of L-alanyl-L-glutamine n-ethanolate by suspending a crystal of L-alanyl-L-glutamine nonhydrate in an aqueous ethanol solution;

(1b) the step of collecting the crystal of L-alanyl-L-glutamine n-ethanolate, which is obtained by the precipitation or the transformation, from the aqueous solution in which the L-alanyl-L-glutamine is dissolved or the aqueous ethanol solution; and (1c) the step of obtaining the crystal of L-alanyl-L-glutamine nonhydrate by ventilation drying the collected crystal of L-alanyl-L-glutamine n-ethanolate.

(13) A method for producing the crystal according to any one of (3) to (5) above, which includes the following steps (2a) to (2c):

(2a) the step of precipitating a crystal of L-alanyl-L-glutamine dihydrate by cooling an aqueous solution, in which L-alanyl-L-glutamine is dissolved, to 35° C. or lower, or by adding or dropping at least one solvent selected from the group consisting of alcohols and ketones into the aqueous solution while keeping the aqueous solution, in which L-alanyl-L-glutamine is dissolved, at 35° C. or lower;

(2b) the step of collecting the precipitated crystal of L-alanyl-L-glutamine dihydrate; and (2c) the step of obtaining a crystal of L-alanyl-L-glutamine nonhydrate by drying the collected crystal of L-alanyl-L-glutamine dihydrate at 40° C. or higher.

(14) A method for producing a crystal of L-alanyl-L-glutamine n-ethanolate, which includes the following steps (1a) and (1b) (wherein, the definition of n is the same as that in (6) above):

(1a) the step of precipitating a crystal of L-alanyl-L-glutamine n-ethanolate by adding or dropping ethanol to an aqueous solution in which L-alanyl-L-glutamine is dissolved, or the step of transforming the crystal of L-alanyl-L-glutamine nonhydrate to a crystal of L-alanyl-L-glutamine n-ethanolate by suspending a crystal of L-alanyl-L-glutamine nonhydrate in an aqueous ethanol solution; and (1b) the step of collecting the crystal of L-alanyl-L-glutamine n-ethanolate, which is obtained by the precipitation or the transformation, from the aqueous solution in which the L-alanyl-L-glutamine is dissolved or the aqueous ethanol solution.

(15) A method for producing a crystal of L-alanyl-L-glutamine dihydrate, which includes the following steps (2a) and (2b):

(2a) the step of precipitating the crystal of L-alanyl-L-glutamine dihydrate by cooling an aqueous solution, in which L-alanyl-L-glutamine is dissolved, to 35° C. or lower, or by adding or dropping at least one solvent selected from the group consisting of alcohols and ketones into the aqueous solution while keeping the aqueous solution, in which L-alanyl-L-glutamine is dissolved, at 35° C. or lower; and (2b) the step of collecting the precipitated crystal of L-alanyl-L-glutamine dihydrate from the aqueous solution.

(16) The production method according to (13) or (15) above, in which the alcohols are at least one alcohol selected from the group consisting of methanol, ethanol, n-propyl alcohol and isopropyl alcohol.

(17) The production method according to (13) or (15) above, in which the ketones are acetone.

Effects of the Invention

The present invention provides a crystal of L-alanyl-L-glutamine having improved powder properties, and a method for producing the same.

EMBODIMENTS FOR CARRYING OUT THE INVENTION

1. Crystal of the Present Invention

Figure 1:
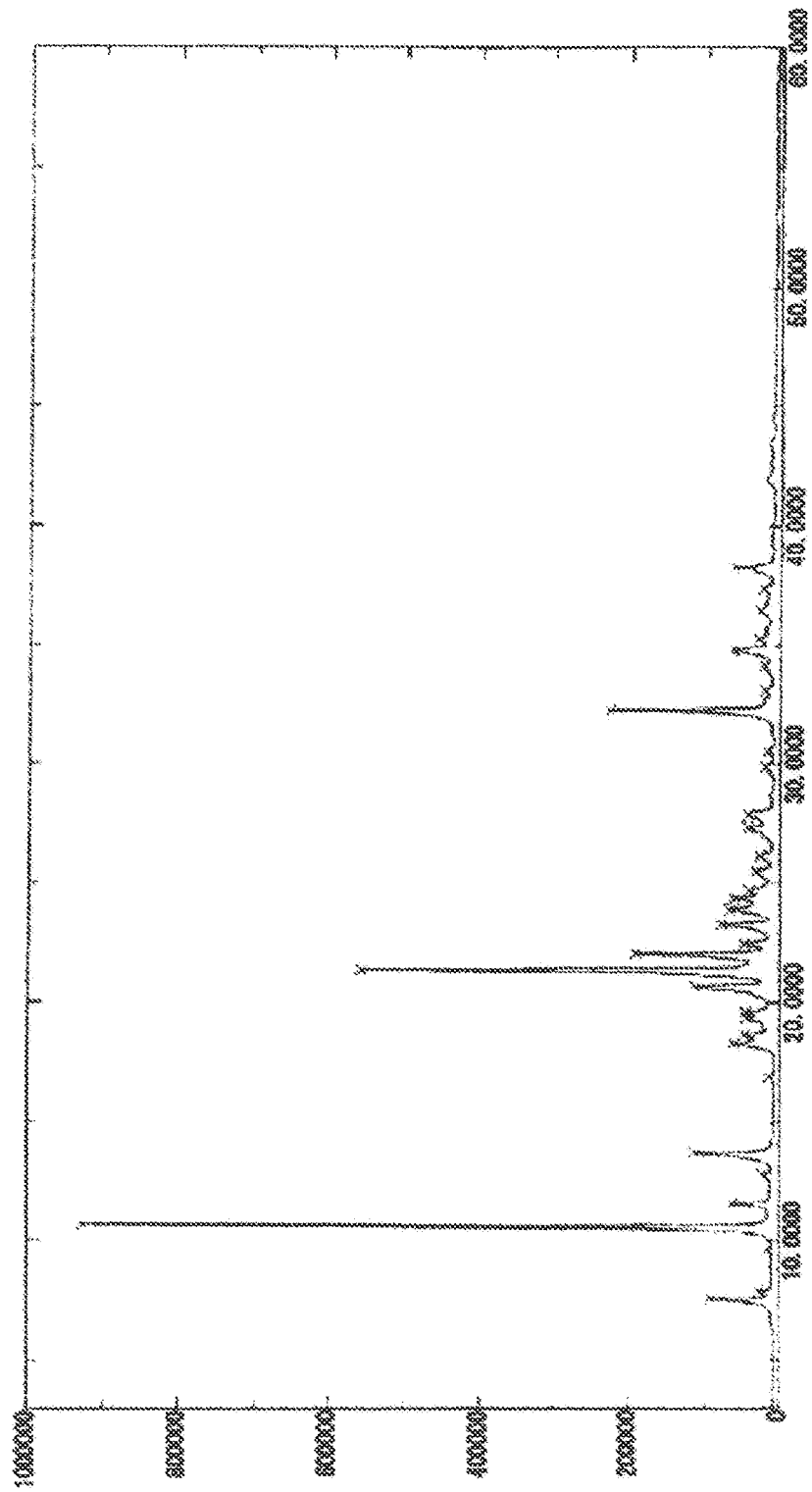
FIG. 1 illustrates results of powder X-ray diffraction of a crystal of L-alanyl-L-glutamine n-ethanolate obtained in Example 1. The vertical axis represents intensity (cps), and the horizontal axis represents a diffraction angle 2θ(°).

The crystal of the present invention is a crystal of L-alanyl-L-glutamine in which the loose specific volume is 5.0 mL/g or less, preferably 4.5 mL/g or less, more preferably 4.0 mL/g or less, and most preferably 3.7 mL/g or less.

L-alanyl-L-glutamine refers to a dipeptide formed by bonding a carboxyl group of L-alanine to an amino group of L-glutamine by a peptide bond.

The loose specific volume refers to a value obtained by dividing volume occupied by a powder by the mass of the powder when a container is filled with the powder and the mass of the powder is measured. A crystal with a low loose specific volume is excellent in filling properties, and easy to handle in various processing steps, and also its transportation cost is low. Therefore, the loose specific volume is preferably low.

The loose specific volume can be measured by a method comprising: dropping crystals to a 50 mL glass measuring cylinder via a two-stage glass funnel to make the volume of the crystal to be about 45 mL, and measuring the weight of the crystals. A value obtained by dividing the measured volume of the crystal by the weight is determined to be the loose specific volume.

In addition, examples of the crystal of the present invention include a crystal of L-alanyl-L-glutamine in which the loose specific volume is 5.0 mL/g or less, and the angle of repose is preferably 50° or less, more preferably 49° or less, still more preferably 48° or less, and most preferably 47° or less.

The angle of repose refers to an angle formed by a generating line of a cone formed with a powder when the powder is allowed to gently fall onto the horizontal plane through a kind of funnel and a horizontal plane.

A crystal having a large angle of repose, when the crystal is discharged from the hopper, cannot be completely discharged from a hopper bottom unless an inclination angle of the hopper bottom is larger than the angle of the repose, and thus, the device is limited and the handling becomes complicated. In addition, the crystal having a large angle of repose is poor in fluidity. Therefore, the angle of repose is preferably small.

The angle of repose can be measured using Multi Tester MT-1001T (manufactured by Seishin Enterprise Co., Ltd.) according to the accompanying manual under the following conditions.

[Measurement Conditions for Angle of Repose]
Used equipment: Multi Tester MT-1001T (manufactured by Seishin Enterprise Co., Ltd.)
Sieve: 1.18 mm
Vibration width: 0.7 to 0.8 mm
Specific example of measurement method for angle of repose: crystals are allowed to fall by passing through a sieve of 1.18 mm that is vibrated with a width of 0.7 to 0.8 mm, and are deposited on an angle-of-repose table (part number: MT-1028). The angle-of-repose table is rotated without being given vibration, angles are read at three sites, and an arithmetic mean value of the angles is determined to be the angle of repose.

As an example of the crystal of the present invention, a crystal of L-alanyl-L-glutamine nonhydrate, a crystal of L-alanyl-L-glutamine n-ethanolate, and a crystal of L-alanyl-L-glutamine dihydrate can be exemplified. Each example is described below.

2. Crystal of L-Alanyl-L-Glutamine Nonhydrate of the Present Invention

As an example of the crystal of the present invention, a crystal of L-alanyl-L-glutamine nonhydrate having a loose specific volume of 5.0 mL/g or less can be exemplified (hereinafter, referred to as a "crystal of L-alanyl-L-glutamine nonhydrate of the present invention").

In addition, as an example of the crystal of L-alanyl-L-glutamine nonhydrate of the present invention, a crystal of L-alanyl-L-glutamine nonhydrate in which the loose specific volume is 5.0 mL/g or less, and the angle of repose is preferably 50° or less can be exemplified.

The crystal of L-alanyl-L-glutamine can be confirmed to be a crystal of nonhydrate when the water content, which is measured by using a thermal analysis according to a method described in the following measurement example, is generally 3.0 wt % or less, preferably 2.5 wt % or less, and more preferably 2.0 wt % or less.

[Measurement Example of Water Content of Crystal according to Thermal Analysis]
Used equipment: EXSTAR 6000 TG/DTA 6200 (manufactured by Seiko Instruments Inc.)
Measurement conditions: Temperature increases from 20° C. to 30° C. at 20° C./min→Hold for 15 minutes at 30° C.→Temperature increases from 30° C. to 250° C. at 5° C./min
Nitrogen flow rate: 300 mL/min
Sampling interval: 0.5 s In addition, as an example of the crystal of L-alanyl-L-glutamine nonhydrate of the present invention, a crystal in which the dense specific volume is preferably 3.0 mL/g or less, and more preferably 2.9 mL/g or less can be exemplified.

The dense specific volume refers to a value obtained by dividing volume of a powder by the mass of the powder, when a container is filled with the powder and the mass of the powder is measured and then a given impact is applied to the container.

The crystal having a low dense specific volume is excellent in filling properties and its transportation cost is low. Therefore, the crystal of L-alanyl-L-glutamine nonhydrate of the present invention preferably has a low dense specific volume.

The dense specific volume can be measured by a method comprising: dropping a crystal to a 50 mL glass measuring cylinder via a two-stage glass funnel to make the volume of the crystal to be about 45 mL; measuring the weight of the crystal; then tapping the measuring cylinder up and down for 100 times; and measuring the volume occupied by the crystal. A value obtained by dividing the measured volume of the crystal by the weight thereof is determined to be the dense specific volume.

In addition, as an example of the crystal of L-alanyl-L-glutamine nonhydrate of the present invention, a crystal in which the difference between the loose specific volume and the dense specific volume is preferably 2.5 mL/g or less, and more preferably 2.0 mL/g or less can be exemplified. A difference between the loose specific volume and the dense specific volume refers to a positive value when the dense specific volume is subtracted from the loose specific volume.

In addition, as an example of the crystal of L-alanyl-L-glutamine nonhydrate of the present invention, a crystal in which the angle of rupture is preferably 45° or less, and more preferably 42° or less can be exemplified.

The angle of rupture refers to an angle formed by a generating line of a cone, formed when a given impact is indirectly applied to a cone formed with a powder by allowing the powder to gently fall onto the horizontal plane through a kind of funnel, and a horizontal plane.

Since the crystal with a large difference between the angle of rupture and the angle of repose is high flowability and are difficult to control, it is preferable that the difference between the angle of rupture and the angle of repose is small.

The angle of rupture can be measured by using Multi Tester MT-1001T (manufactured by Seishin Enterprise Co., Ltd.) according to the accompanying manual with the method described in the following specific example.

[Specific Example of Measurement Method for Angle of Rupture]
The angle of repose is measured, and then the weight attached to the bottom of the angle-of-repose table unit (part number: MT-1028) is slowly lift under a tapping table and allowed to fall. The operation is repeated for three times. Angles are read at three sites by a method similar to the measurement method for the angle of repose, and an arithmetic mean value of the angles is determined to be the angle of rupture.

In addition, as an example of the crystal of L-alanyl-L-glutamine nonhydrate of the present invention, the crystal, which has peaks at an angle of diffraction ($2\theta°$) described in the following (x1) in powder X-ray diffraction using CuKα as an X-ray source, is preferred, and the crystal, which further has peaks at an angle of diffraction ($2\theta°$) described in the following (x2) in addition to the following (x1) in the powder X-ray diffraction, is more preferred.

(x1) 13.7°±0.2°, preferably ±0.1°, 20.7°±0.2°, preferably ±0.1°, and 34.9°±0.2°, preferably ±0.1°

(x2) 21.5°±0.2°, preferably ±0.1°, and 22.3°±0.2°, preferably ±0.1°

As an example of the crystal of L-alanyl-L-glutamine nonhydrate of the present invention, more specifically, the crystals which has the powder X-ray diffraction patterns, using CuKα as the X-ray source, is defined by the patterns shown in FIGS. 4, 8, 9, and 10, and by the values of diffraction angles shown in Tables 7, 14, 15, and 16, can be exemplified. The powder X-ray diffraction can be performed according to the method described in the following measurement examples.

[Measurement Example of Powder X-ray Diffraction]

Used equipment: Device of powder X-ray diffraction (XRD) Ultima IV (manufactured by Rigaku Corporation)

Anode: Cu

Wavelength: 1.5418 Å

3. Crystal of L-Alanyl-L-Glutamine n-Ethanolate of the Present Invention

As an example of the crystal of the present invention, a crystal of L-alanyl-L-glutamine n-ethanolate of the present invention having a loose specific volume of 5.0 mL/g or less can be exemplified (hereinafter, referred to as a "crystal of L-alanyl-L-glutamine n-ethanolate of the present invention").

The crystal of L-alanyl-L-glutamine n-ethanolate refers to a crystal of a compound that is formed by coordination of n ethanol molecules to one L-alanyl-L-glutamine molecule. In the crystal of L-alanyl-L-glutamine n-ethanolate of the present invention, n represents any number greater than 0, preferably any number greater than 0 and equal to or smaller than 5, more preferably any number greater than 0 and equal to or smaller than 3, still more preferably any number greater than 0 and equal to or smaller than 1, particularly preferably any number rounded up to the first decimal place that is greater than 0 and equal to or smaller than 1, and most preferably any number rounded up to the second decimal place that is greater than 0 and equal to or smaller than 1.

The crystal of L-alanyl-L-glutamine can be confirmed to be a crystal of n-ethanolate when the ethanol content of the crystal of L-alanyl-L-glutamine, which is measured by using gas chromatograph according to the method described in the following analysis example, is generally 0.5 to 16 wt %, preferably 3.0 to 16 wt %, and more preferably 5.0 to 16 wt %.

[Analysis Example Using Gas Chromatograph]

Used equipment: GC-2014 (manufactured by Shimadzu Corporation)

Column filler: Adsorb P-1 60/80 mesh (manufactured by Nishio Kogyo Co., Ltd.)

Column temperature: 120° C.

Vaporization chamber temperature: 150° C.

Helium flow rate: 30 mL/min

Detector temperature: 220° C.

Sample preparation method: About 1.0 g of a crystal of L-alanyl-L-glutamine n-ethanolate is weighed and dissolved in distilled water, and the mixture is adjusted to a 10 mL solution and is used as a sample.

As the ethanol content and the value of n in the crystal of L-alanyl-L-glutamine n-ethanolate of the present invention, specifically, the ethanol contents and the values of n shown in Table 6 can be exemplified.

In addition, as an example of the crystal of L-alanyl-L-glutamine n-ethanolate of the present invention, a crystal in which the loose specific volume is 5.0 mL/g or less, and the angle of repose is preferably 50° or less can be exemplified.

In addition, as an example of the crystal of L-alanyl-L-glutamine n-ethanolate of the present invention, a crystal in which the dense specific volume is preferably 3.0 mL/g or less, and more preferably 2.5 mL/g or less can be exemplified.

In addition, as an example of the crystal of L-alanyl-L-glutamine n-ethanolate of the present invention, a crystal in which the difference between the loose specific volume and the dense specific volume is preferably 2.0 mL/g or less, and more preferably 1.5 mL/g or less can be exemplified.

In addition, as an example of the crystal of L-alanyl-L-glutamine n-ethanolate of the present invention, a crystal in which the angle of rupture is preferably 45° or less, and more preferably 40° or less can be exemplified.

In addition, as an example of the crystal of L-alanyl-L-glutamine n-ethanolate of the present invention, the crystal, which has peaks at an angle of diffraction (2θ°) described in the following (y1) in powder X-ray diffraction using CuKα as the X-ray source and as an anode, is preferred, and the crystal, which further has peaks at an angle of diffraction (2θ°) described in the following (y2) in addition to the following (y1) in the powder X-ray diffraction, is more preferred.

(y1) 10.7°±0.2°, preferably ±0.1°, 20.7°±0.2°, preferably ±0.1°, 21.4°±0.2°, preferably ±0.1°, 23.3°±0.2°, preferably ±0.1°, and 34.8°±0.2°, preferably ±0.1°

(y2) 18.4±0.2°, preferably ±0.1°, 24.7±0.2°, preferably ±0.1°, 27.9±0.2°, preferably ±0.1°, and 32.3±0.2°, preferably ±0.1°

Figure 2:
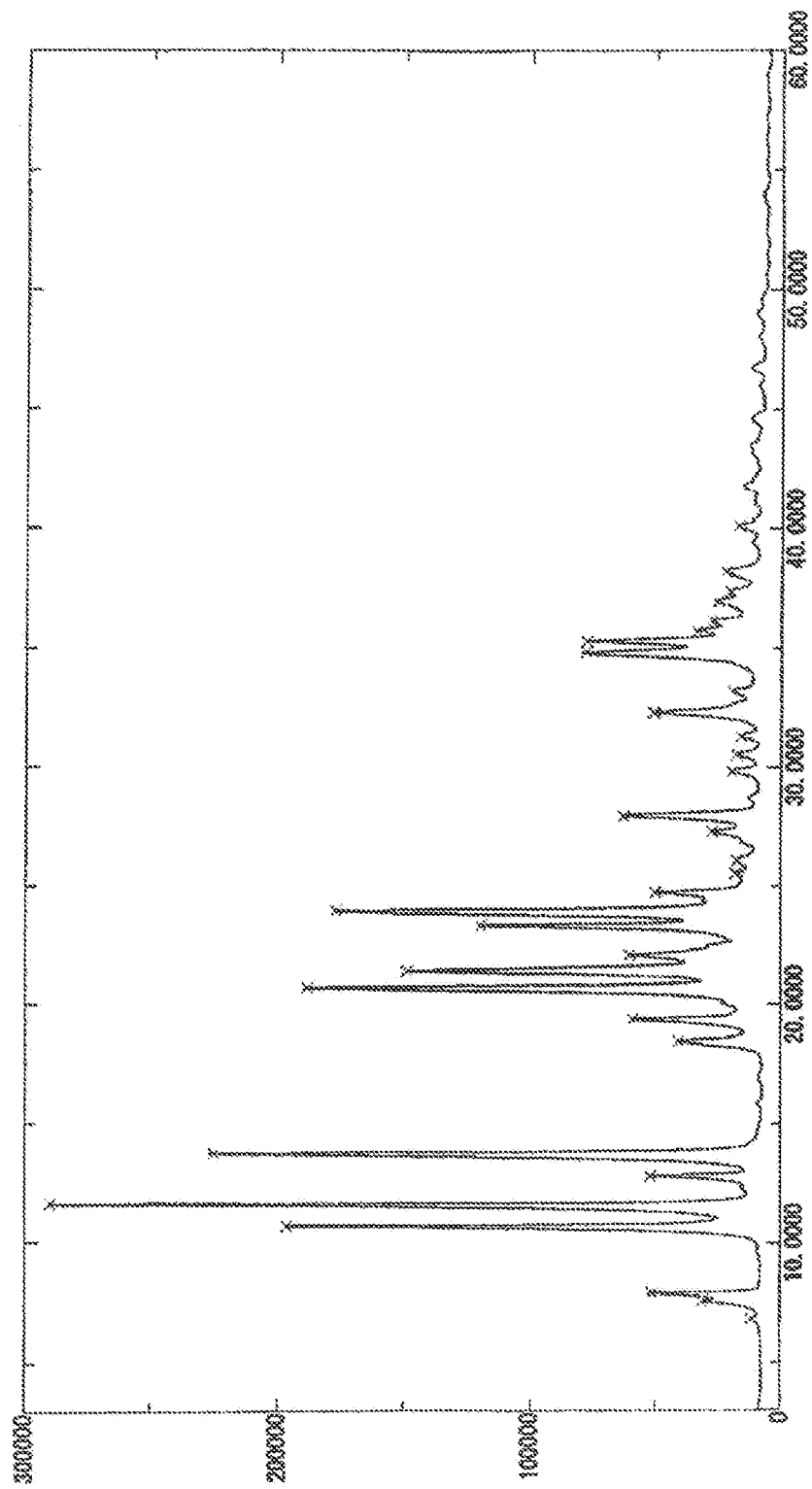
FIG. 2 illustrates results of powder X-ray diffraction of a crystal of L-alanyl-L-glutamine n-ethanolate obtained in Example 2 (vacuum drying at 95° C. for 6 hours). The vertical axis represents intensity (cps), and the horizontal axis represents a diffraction angle 2θ (°).
Figure 3:
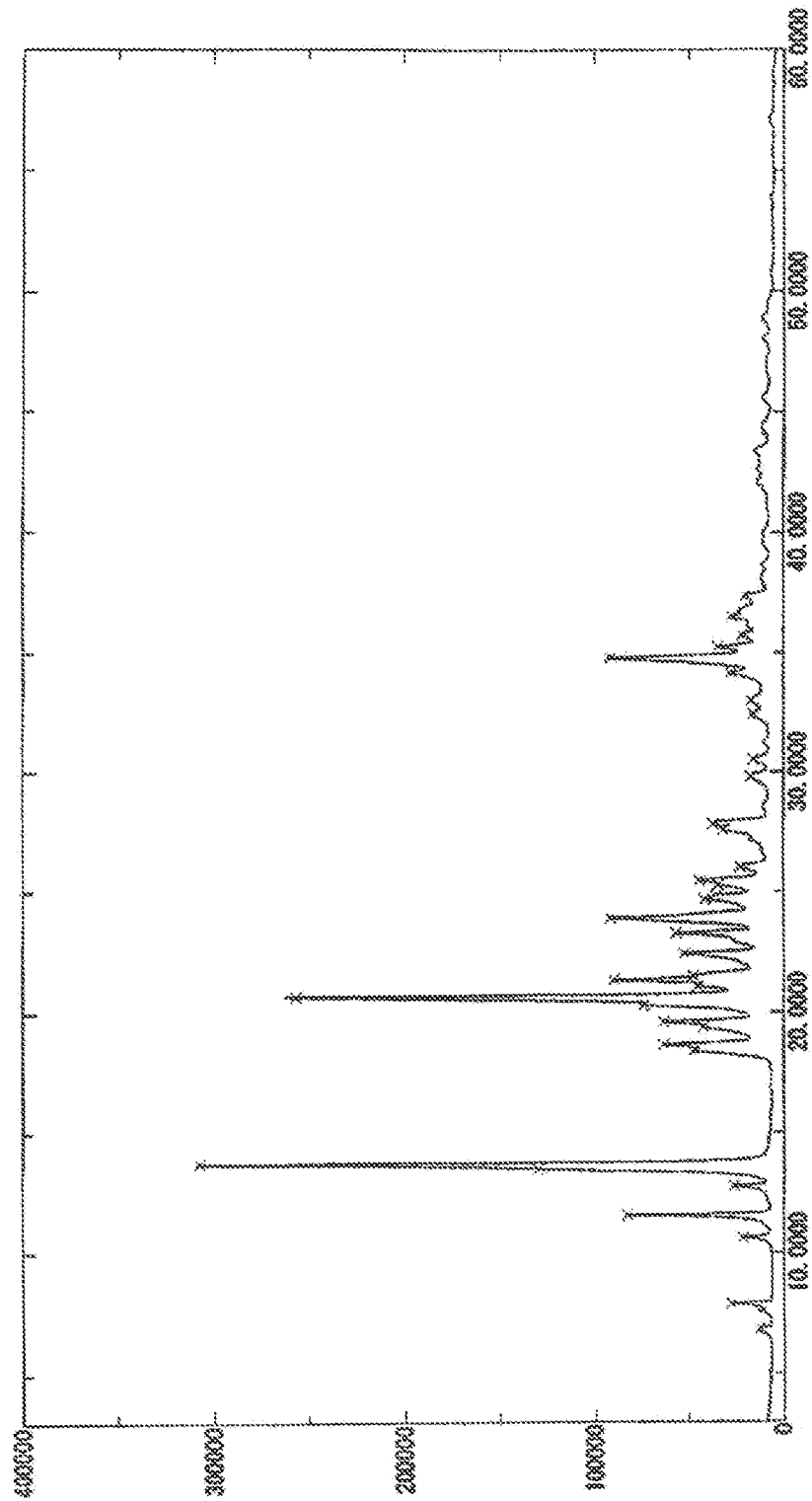
FIG. 3 illustrates results of powder X-ray diffraction of a crystal of L-alanyl-L-glutamine n-ethanolate obtained in Example 3. The vertical axis represents intensity (cps), and the horizontal axis represents a diffraction angle 2θ (°).
Figure 4:
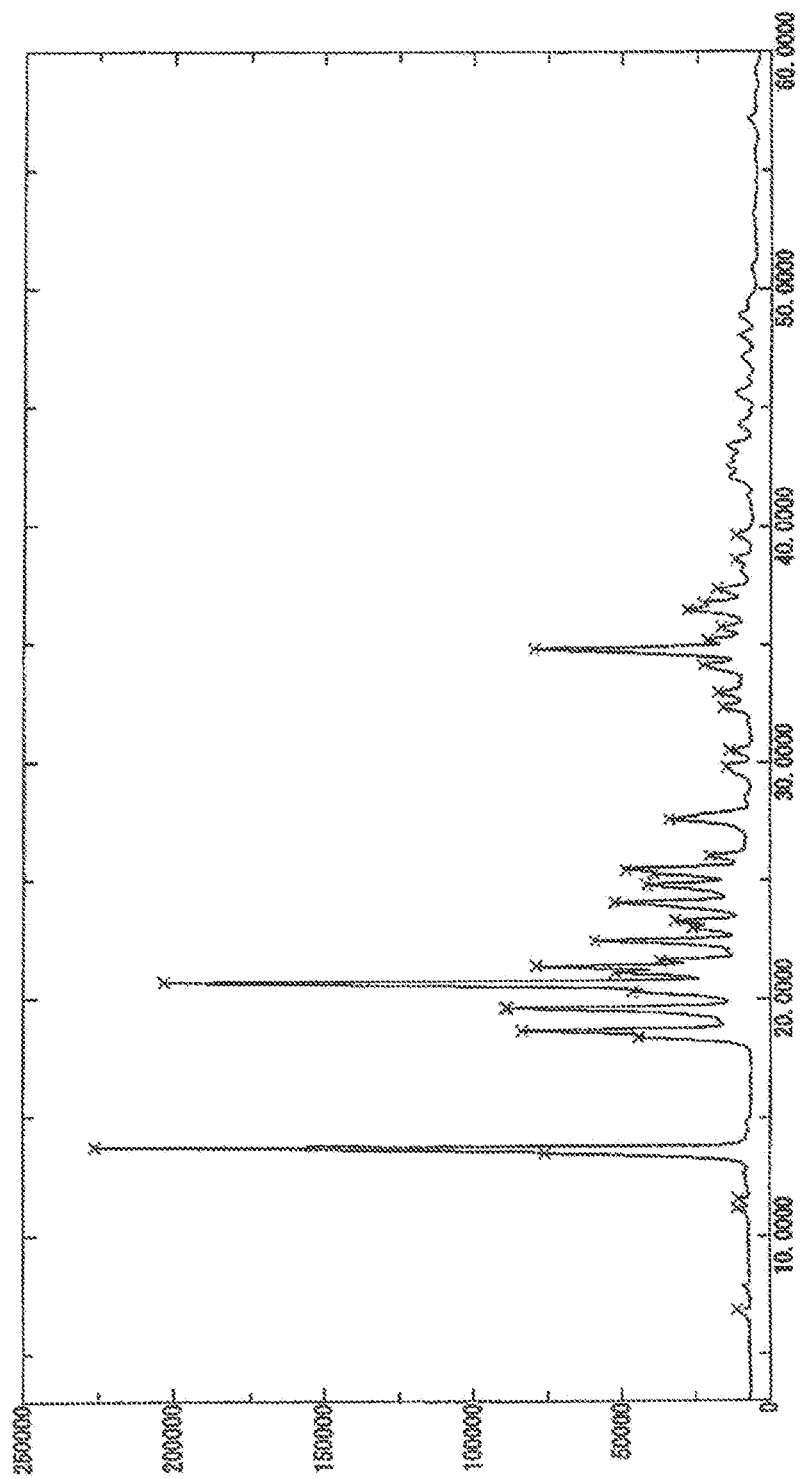
FIG. 4 illustrates results of powder X-ray diffraction of a crystal of L-alanyl-L-glutamine nonhydrate obtained in Example 5. The vertical axis represents intensity (cps), and the horizontal axis represents a diffraction angle 2θ (°).

As an example of the crystal of L-alanyl-L-glutamine n-ethanolate of the present invention, more specifically, crystals of which the powder X-ray diffraction patterns in which CuKα is used as the X-ray source and as an anode, are defined by the patterns shown in FIGS. 1, 2, and 3, as well as defined by the values of diffraction angles shown in Tables 2, 3, and 4 can be exemplified.

The powder X-ray diffraction pattern of the crystal can also be calculated from a single-crystal structure by simulation. As a method for determining the single crystal structure, a structure analysis according to a single crystal X-ray analysis can be exemplified. For example, a single crystal of n-ethanolate of L-alanyl-L-glutamine is placed in a diffractometer, a diffraction image of the single crystal is measured in atmosphere at room temperature or in an inert gas flow at predetermined temperature by using an X-ray with a predetermined wavelength, and the structure is determined by a direct method and refined by a least squares method based on a combination of the image index and diffraction intensity calculated from the diffraction image, so as to obtain a single crystal structure. Specifically, for example, a single crystal structure can be obtained using R-AXIS RAPID-F (manufactured by Rigaku Corporation) according to an instruction manual.

As a method for simulating a powder X-ray diffraction pattern from a single-crystal structure, for example, the crystal structure display program Mercury (Cambridge crystallographic data center) or the PowderCell (Federal Material Research Laboratory) can be used. The powder X-ray diffraction pattern can be calculated by inputting a lattice constant and atomic coordinates of the crystal, and a wavelength of the X-ray used for the calculation.

4. Crystal of L-Alanyl-L-Glutamine Dihydrate of the Present Invention

As an example of the crystal of the present invention, a crystal of L-alanyl-L-glutamine dihydrate having a loose specific volume of 5.0 mL/g or less can be exemplified (hereinafter, also referred to as a "crystal of L-alanyl-L-glutamine dihydrate of the present invention").

L-alanyl-L-glutamine dihydrate refers to a compound formed by coordination of two water molecules to one L-alanyl-L-glutamine molecule.

The crystal of L-alanyl-L-glutamine can be confirmed to be a crystal of dihydrate when the water content, which is measured by using a Karl-Fischer method described in the following measurement example, is generally 8 to 20 wt %, preferably 10 to 18 wt %, and more preferably 12 to 16 wt %.

[Measurement Example of Water Content of Crystals according to Karl-Fischer Method]

Used equipment: MKA-510N/MKS-510N (manufactured by Kyoto Electronics Manufacturing Co., Ltd.)

Specific example of measurement method: The water content of the crystal is measured according to an instruction manual of MKA-510N/MKS-510N (manufactured by Kyoto Electronics Manufacturing Co., Ltd.).

In addition, as an example of the crystal of L-alanyl-L-glutamine dihydrate of the present invention, a crystal of L-alanyl-L-glutamine dihydrate in which the loose specific volume is 5.0 mL/g or less, and the angle of repose is preferably 50° or less can be exemplified.

In addition, as an example of the crystal of L-alanyl-L-glutamine dihydrate of the present invention, a crystal in which the dense specific volume is preferably 3.0 mL/g or less, and more preferably 2.8 mL/g or less can be exemplified.

In addition, as an example of the crystal of L-alanyl-L-glutamine dihydrate of the present invention, a crystal in which the difference between the loose specific volume and the dense specific volume is preferably 2.0 mL/g or less, and more preferably 1.0 mL/g or less can be exemplified.

In addition, as an example of the crystal of L-alanyl-L-glutamine dihydrate of the present invention, a crystal in which the angle of rupture is preferably 45° or less, and more preferably 40° or less can be exemplified.

In addition, as an example of the crystal of L-alanyl-L-glutamine dihydrate of the present invention, the crystal, which has peaks at an angle of diffraction ($2\theta°$) described in the following (z1) in powder X-ray diffraction using CuK$\alpha$ as the X-ray source and as an anode, is preferred, and the crystal, which further has peaks at an angle of diffraction ($2\theta°$) described in the following (z2) in addition to the following (z1) in the powder X-ray diffraction, is more preferred.

(z1) 11.6°±0.2°, preferably ±0.1°, 23.3°±0.2°, preferably ±0.1°, 23.9°±0.2°, preferably ±0.1°, 27.9°±0.2°, preferably ±0.1°, and 35.3°±0.2°, preferably +0.1°

(z2) 7.9°±0.2°, preferably ±0.1°, 12.8°±0.2°, preferably ±0.1°, 18.3° 0.2°, preferably ±0.1°, 21.6°±0.2°, preferably ±0.1°, and 24.7°+0.2°, preferably ±0.1°

Figure 5:
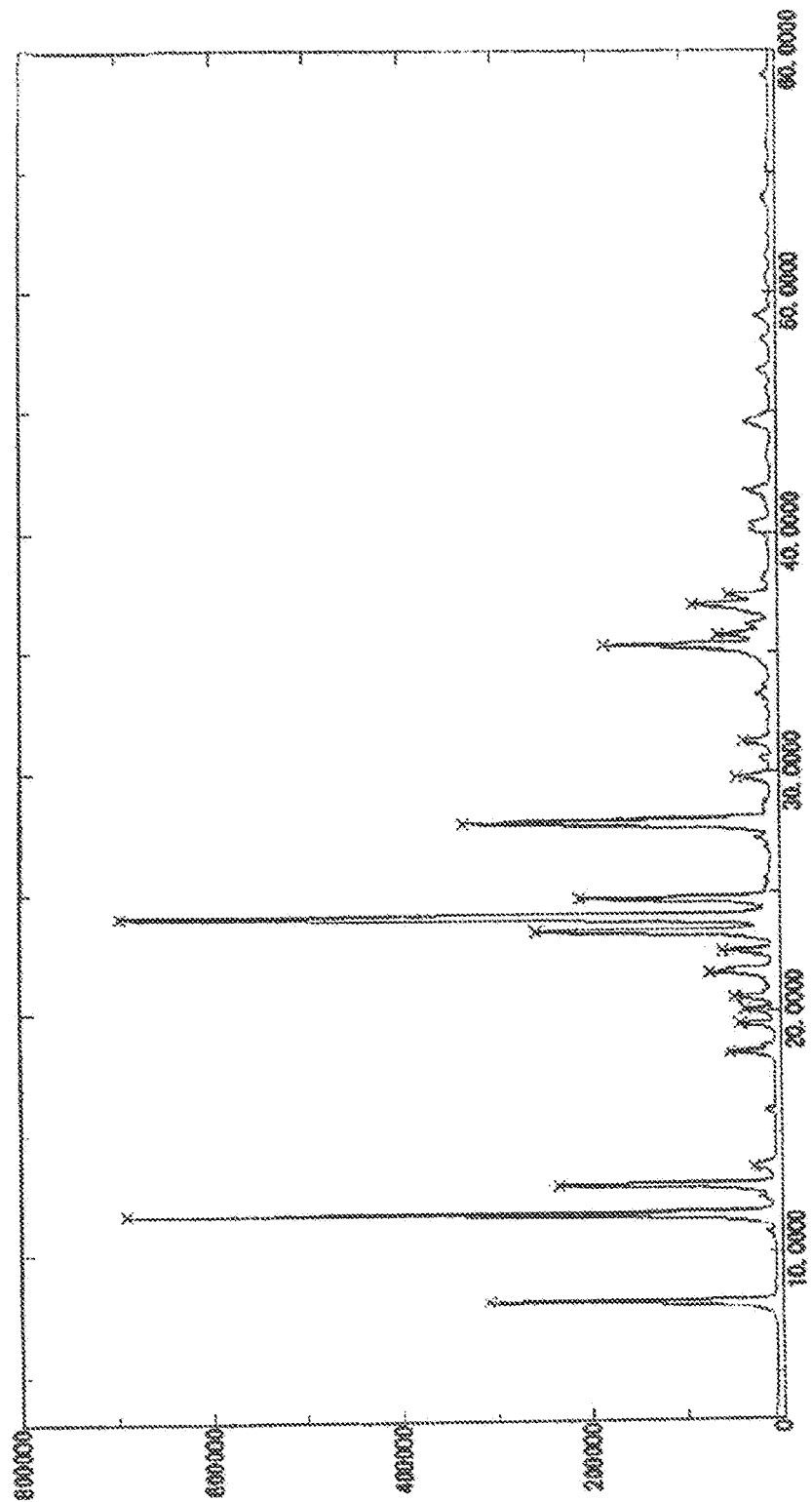
FIG. 5 illustrates results of powder X-ray diffraction of a crystal of L-alanyl-L-glutamine dihydrate obtained in Example 6. The vertical axis represents intensity (cps), and the horizontal axis represents a diffraction angle 2θ (°).
Figure 6:
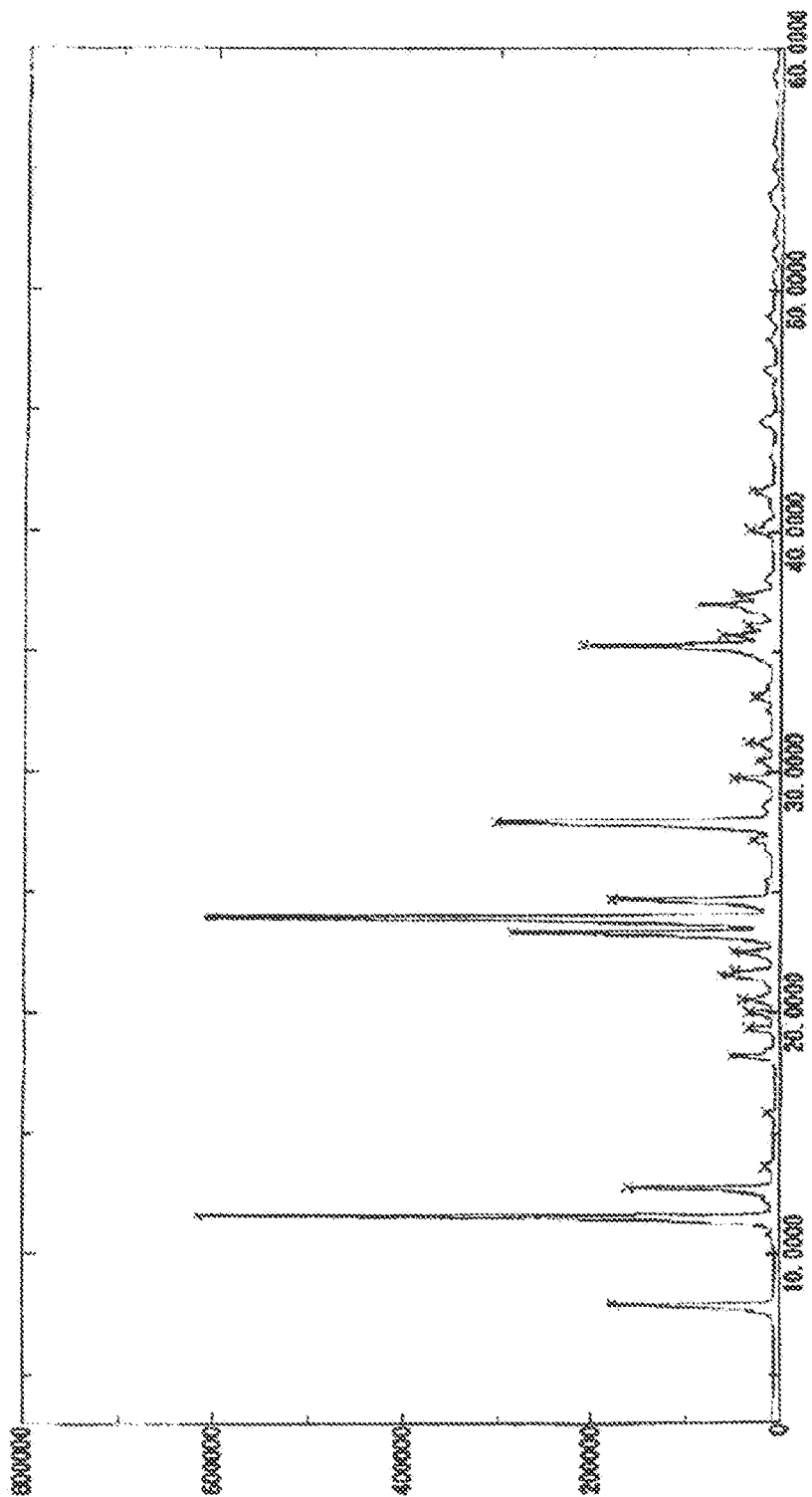
FIG. 6 illustrates results of powder X-ray diffraction of a crystal of L-alanyl-L-glutamine dihydrate obtained in Example 8. The vertical axis represents intensity (cps), and the horizontal axis represents a diffraction angle 2θ (°).
Figure 7:
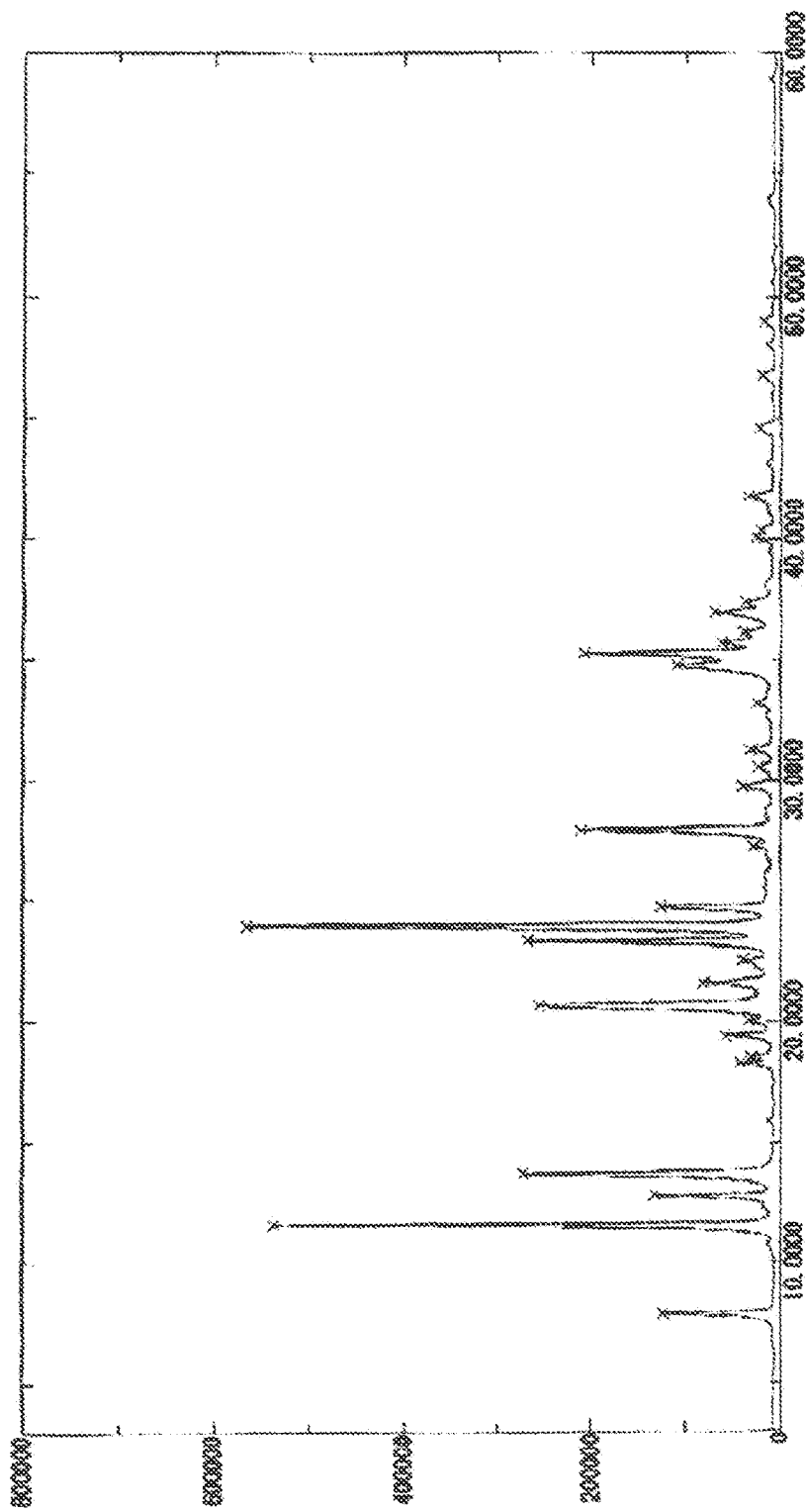
FIG. 7 illustrates results of powder X-ray diffraction of a crystal of L-alanyl-L-glutamine dihydrate obtained in Example 9. The vertical axis represents intensity (cps), and the horizontal axis represents a diffraction angle 2θ (°).
Figure 8:
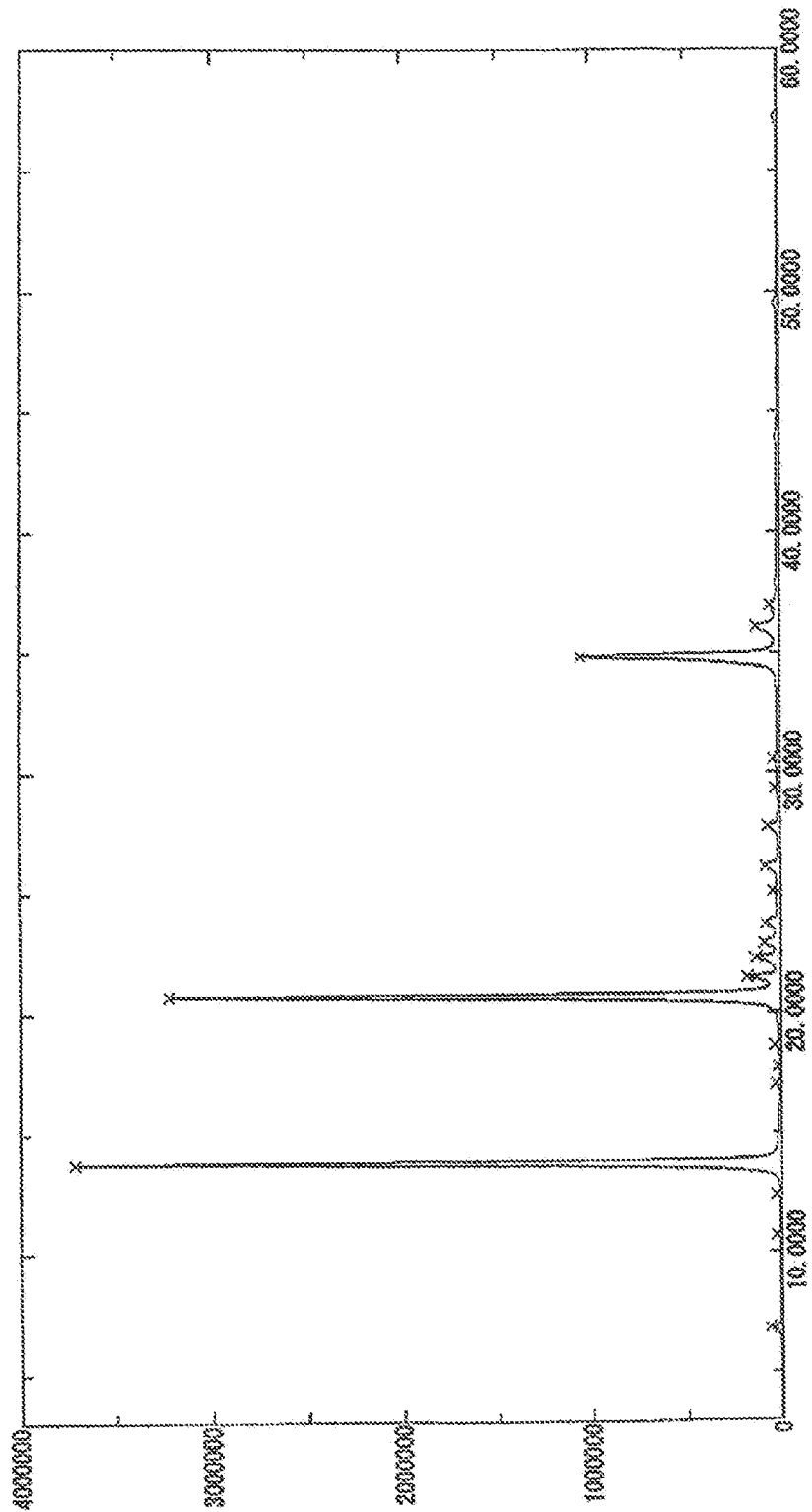
FIG. 8 illustrates results of powder X-ray diffraction of a crystal of L-alanyl-L-glutamine nonhydrate obtained in Example 10. The vertical axis represents intensity (cps), and the horizontal axis represents a diffraction angle 2θ (°).
Figure 9:
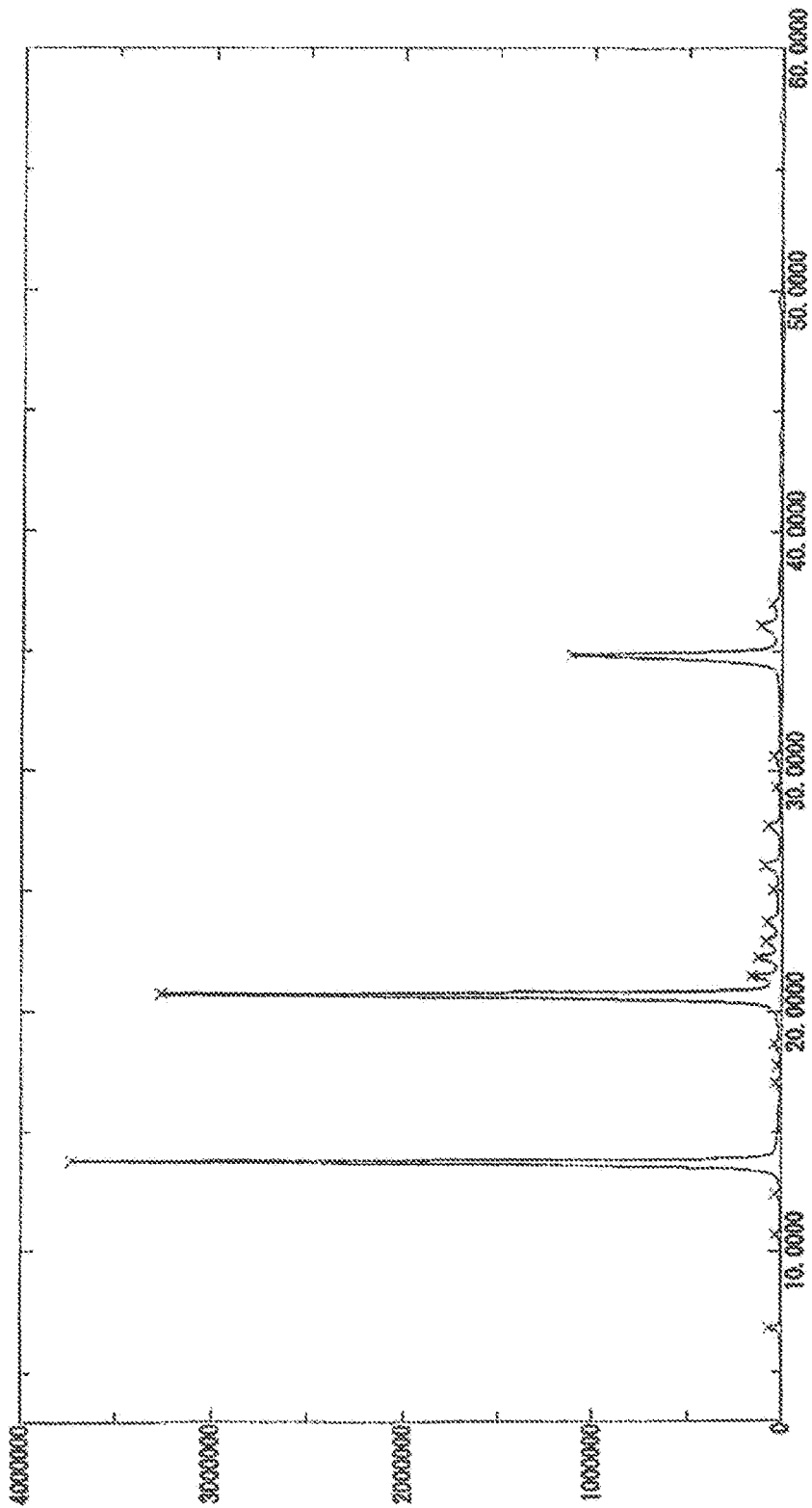
FIG. 9 illustrates results of powder X-ray diffraction of a crystal of L-alanyl-L-glutamine nonhydrate obtained in Example 11. The vertical axis represents intensity (cps), and the horizontal axis represents a diffraction angle 2θ (°).
Figure 10:
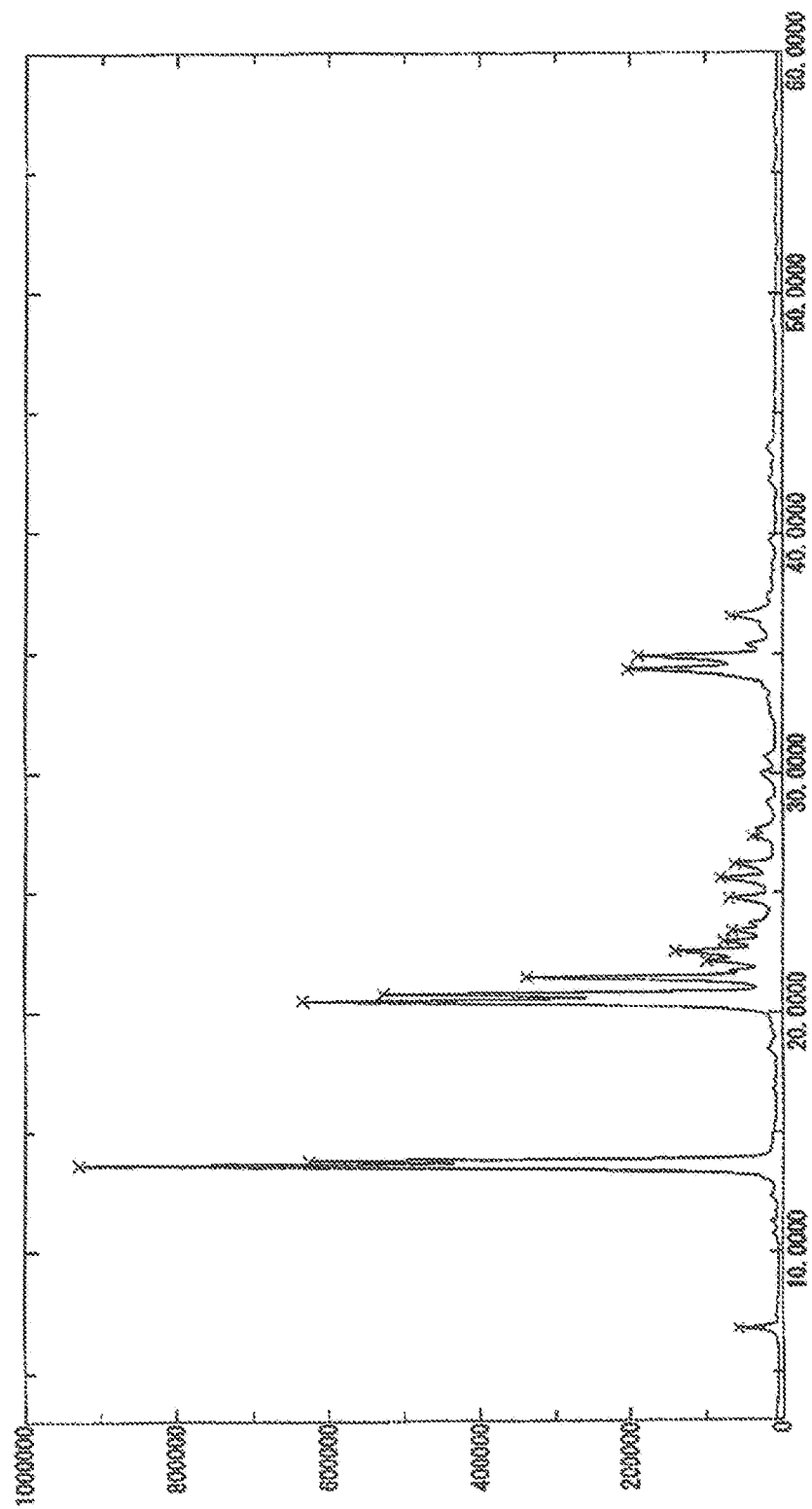
FIG. 10 illustrates results of powder X-ray diffraction of a crystal of L-alanyl-L-glutamine nonhydrate obtained in Example 12. The vertical axis represents intensity (cps), and the horizontal axis represents a diffraction angle 2θ (°).

As an example of the crystal of L-alanyl-L-glutamine dihydrate of the present invention, more specifically, a crystal of L-alanyl-L-glutamine dihydrate of which the powder X-ray diffraction patterns, in which CuK$\alpha$ is used as the X-ray source and as an anode, is defined by the patterns shown in FIGS. 5, 6, and 7, and by the values of diffraction angles shown in Tables 10, 12, and 13 can be exemplified.

In addition, the powder X-ray diffraction pattern of the crystal of L-alanyl-L-glutamine dihydrate of the present invention can be calculated from a single crystal structure by simulation, based on a method similar to that of 3 above.

5. Method for Producing Crystal of L-Alanyl-L-Glutamine Nonhydrate of the Present Invention, Crystal of L-Alanyl-L-Glutamine n-Ethanolate of the Present Invention, and Crystal of L-Alanyl-L-Glutamine Dihydrate of the Present Invention As a method for producing the crystal of L-alanyl-L-glutamine n-ethanolate of the present invention, a production method described in 5.1 below can be exemplified. As a method for producing the crystal of L-alanyl-L-glutamine dihydrate of the present invention, a production method described in 5.2 below can be exemplified. As a method for producing the crystal of L-alanyl-L-glutamine nonhydrate of the present invention, a production method described in 5.3 or 5.4 below can be exemplified.

5.1 Method for Producing Crystal of L-Alanyl-L-Glutamine n-Ethanolate of the Present Invention The method for producing the crystal of L-alanyl-L-glutamine n-ethanolate of the present invention comprises the following steps (1a) and (1b).

(1a) the step of precipitating a crystal of L-alanyl-L-glutamine n-ethanolate by adding or dropping ethanol to an aqueous solution in which L-alanyl-L-glutamine is dissolved, or the step of transforming the crystal of L-alanyl-L-glutamine nonhydrate to a crystal of L-alanyl-L-glutamine n-ethanolate by suspending a crystal of L-alanyl-L-glutamine nonhydrate in an aqueous ethanol solution;

(1b) the step of collecting the crystal of L-alanyl-L-glutamine n-ethanolate, which is obtained by the precipitation or the transformation, from the aqueous solution in which the L-alanyl-L-glutamine is dissolved or the aqueous ethanol solution 5.1.1 Step (1a)

The L-alanyl-L-glutamine contained in the aqueous solution in which L-alanyl-L-glutamine is dissolved may be produced by any of a fermentation method, an enzyme method, a method for extracting L-alanyl-L-glutamine from a natural substance, a chemical synthesis method, or the like.

When the aqueous solution in which L-alanyl-L-glutamine is dissolved contains solids that interfere with crystallization, the solids can be removed by using centrifugation, filtration, ceramic filters, or the like.

In addition, when the aqueous solution in which L-alanyl-L-glutamine is dissolved contains water-soluble impurities or salts that interfere with crystallization, the impurities or salts in the aqueous solution can be removed by being passed through a column filled with an ion exchange resin or the like.

In addition, when the aqueous solution in which L-alanyl-L-glutamine is dissolved contains hydrophobic impurities that interfere with crystallization, the hydrophobic impurities can be removed by being passed through a column filled with a synthetic adsorption resin, activated carbon, or the like.

As a concentration of L-alanyl-L-glutamine in an aqueous solution in which L-alanyl-L-glutamine is dissolved, generally 300 g/L or more, preferably 400 g/L or more, and most preferably 450 g/L or more can be exemplified.

As a condition during addition or dropping of ethanol, the condition, in which the aqueous solution in which L-alanyl-L-glutamine is dissolved is generally maintained at 10 to 50° C., preferably 15 to 50° C., and most preferably 20 to 50° C., and ethanol whose volume generally equal to 1 to 5 times the volume of the aqueous solution, preferably equal to 1 to 3 times the volume thereof, and most preferably equal to 1 to 2 times the volume thereof is added or dropped generally over 1 to 24 hours, preferably over 1 to 20 hours, and most preferably over 1 to 16 hours, can be exemplified.

In the method for producing the crystal of L-alanyl-L-glutamine n-ethanolate of the present invention, a crystal of L-alanyl-L-glutamine n-ethanolate may be added as a seed crystal before the crystal of L-alanyl-L-glutamine n-ethanolate is precipitated, so that the concentration of L-alanyl-L-glutamine n-ethanolate in the aqueous solution is generally 0.2 to 25 g/L, preferably 0.5 to 10 g/L, and most preferably 2 to 5 g/L.

As time for adding the seed crystal, generally 1 to 5 hours, preferably 1 to 4 hours, and most preferably 1 to 3 hours after the start of dropping or addition of ethanol can be exemplified.

After precipitating the crystal of L-alanyl-L-glutamine n-ethanolate as described above, further, the precipitated crystal can be generally cooled to 5 to 25° C., preferably 5 to 20° C., and most preferably 5 to 15° C., and can be aged for 1 to 48 hours, preferably for 1 to 24 hours, and most preferably for 1 to 12 hours.

Aging a crystal refers to growing the crystal by stopping the step of adding or dropping ethanol.

Growing a crystal refers to increasing the crystal based on the precipitated crystal.

Aging of the crystal is mainly performed to grow the crystal, but a new crystal may be precipitated simultaneously with the growth of the crystal.

After aging the crystals, the step of adding or dropping ethanol may be resumed.

In addition, the crystal of L-alanyl-L-glutamine n-ethanolate of the present invention can be also obtained by suspending the crystal of L-alanyl-L-glutamine nonhydrate in the aqueous ethanol solution to transform the crystal of L-alanyl-L-glutamine nonhydrate to the crystal of L-alanyl-L-glutamine n-ethanolate.

The crystal of L-alanyl-L-glutamine nonhydrate can be obtained according to a method described in Japanese Patent No. 4931801.

The crystal of L-alanyl-L-glutamine nonhydrate is suspended in an aqueous ethanol solution whose weight percentage is generally 10 to 90 wt %, preferably 20 to 80 wt %, and most preferably 30 to 70 wt % so as to make the concentration to be generally 300 to 800 g/L, preferably 400 to 750 g/L, and most preferably 500 to 700 g/L, and is left to stand or is suspended generally at 10 to 40° C., preferably at 15 to 40° C., and most preferably at 20 to 40° C., generally for 4 to 32 hours, preferably for 8 to 28 hours, and most preferably 12 to 24 hours, and then the crystal of L-alanyl-L-glutamine nonhydrate can be transformed to the crystal of L-alanyl-L-glutamine n-ethanolate.

5.1.2 Step (1b)

In the step of collecting the crystal of L-alanyl-L-glutamine n-ethanolate of the present invention from an aqueous solution, although not particularly limited, pressure filtration, suction filtration, centrifugation, or the like can be performed. Furthermore, the crystal can be appropriately washed in order to reduce the adhesion of the mother liquor and then improve the quality of the crystal.

The solution used for crystal washing is not particularly limited, and, for example, water, methanol, ethanol, acetone, n-propanol, isopropyl alcohol, and a mixture of one or more selected from them in any ratio can be used.

The crystal of L-alanyl-L-glutamine n-ethanolate according to the present invention can be obtained by drying the wet crystal obtained as described above.

As the drying conditions of the wet crystal, any method can be used as long as the method can retain the crystal of L-alanyl-L-glutamine n-ethanolate, for example, vacuum drying can be applied, however, ventilation drying cannot be used in the present step since it cannot retain the crystal of L-alanyl-L-glutamine n-ethanolate. The drying temperature can be any temperature as long as the temperature is in a range at which attached water can be removed, and generally 10 to 95° C., and more preferably 20 to 60° C.

As drying time, generally 4 to 36 hours, preferably 5 to 24 hours, and most preferably 6 to 16 hours can be exemplified.

5.2 Method for Producing Crystal of L-Alanyl-L-Glutamine Dihydrate of the Present Invention The method for producing the crystal of L-alanyl-L-glutamine dihydrate of the present invention comprises the following steps (2a) and (2b).

(2a) the step of precipitating the crystal of L-alanyl-L-glutamine dihydrate by cooling the aqueous solution, in which L-alanyl-L-glutamine is dissolved, to 35° C. or lower, or by adding or dropping a solvent selected from the group consisting of alcohols and ketones into the aqueous solution while keeping the aqueous solution, in which L-alanyl-L-glutamine is dissolved, at 35° C. or lower;

(2b) the step of collecting the precipitated crystal of L-alanyl-L-glutamine dihydrate from the aqueous solution 5.2.1 Step (2a)

L-Alanyl-L-glutamine contained in the aqueous solution in which L-alanyl-L-glutamine is dissolved can be produced by a method similar to that of 5.1.1 above.

The method similar to that of 5.1.1 above can be used; when the aqueous solution in which L-alanyl-L-glutamine is dissolved contains solids that interfere with crystallization; when the aqueous solution contains water-soluble impurities or salts that interfere with crystallization; and when the aqueous solution contains hydrophobic impurities that interfere with crystallization.

The crystal of L-alanyl-L-glutamine dihydrate can be precipitating by cooling the aqueous solution, in which L-alanyl-L-glutamine is dissolved, to 35° C. or lower, preferably 30° C. or lower, and more preferably 25° C. or lower.

As a concentration of L-alanyl-L-glutamine in the aqueous solution in which L-alanyl-L-glutamine is dissolved, generally 300 g/L or more, preferably 400 g/L or more, and most preferably 450 g/L or more can be exemplified.

Instead of the above method or after precipitating the crystal of L-alanyl-L-glutamine dihydrate by the above method, further, the crystal of L-alanyl-L-glutamine dihydrate can be precipitated by adding a solvent selected from the group consisting of alcohols and ketones while keeping the aqueous solution at 35° C. or lower, preferably 30° C. or lower, and more preferably 25° C. or lower.

As the alcohols, preferably alcohols selected from the group consisting of methanol, ethanol, n-propanol and isopropyl alcohol, more preferably alcohols selected from the group consisting of methanol, ethanol and isopropyl alcohol, and most preferably isopropyl alcohol can be exemplified.

As the ketones, preferably acetone can be exemplified.

As an amount of the solvent selected from the group consisting of alcohols and ketones to be added or dropped, generally 1 to 5 times, preferably 1 to 3 times, and most preferably 1 to 2 times the amount of the aqueous solution in which L-alanyl-L-glutamine is dissolved can be exemplified.

As time required for adding or dropping the solvent selected from the group consisting of alcohols and ketones, generally 1 to 12 hours, preferably 2 to 11 hours, and most preferably 3 to 10 hours can be exemplified.

In the method for producing the crystal of L-alanyl-L-glutamine dihydrate of the present invention, the crystal of L-alanyl-L-glutamine dihydrate may be added as a seed crystal before the crystal of L-alanyl-L-glutamine dihydrate is precipitated, so that the concentration of L-alanyl-L- glutamine in the aqueous solution is generally 0.2 to 25 g/L, preferably 0.5 to 10 g/L, and most preferably 2 to 5 g/L.

After the crystal of L-alanyl-L-glutamine dihydrate is precipitated as described above, furthermore, the precipitated crystal can be generally aged at 0 to 40° C., preferably at 5 to 35° C., and most preferably at 10 to 30° C. generally for 1 to 48 hours, preferably for 1 to 24 hours, and most preferably for 1 to 12 hours.

After aging the crystal, the step of adding or dropping the solvent selected from the group consisting of alcohols and ketones may be resumed.

5.2.2 Step (2b)

In the step of collecting the crystal of L-alanyl-L-glutamine dehydrate precipitated from the aqueous solution in the above step (2a), although not particularly limited, pressure filtration, suction filtration, centrifugation, or the like can be performed. Furthermore, the crystal can be appropriately washed in order to reduce the adhesion of the mother liquor and then improve the quality of the crystal. The solution used for crystal washing is not particularly limited, and, for example, water, methanol, ethanol, acetone, n-propanol, isopropyl alcohol, and a mixture of one or more selected from them in any ratio can be used.

The crystal of L-alanyl-L-glutamine dihydrate of the present invention can be obtained by drying the wet crystal obtained as described above.

As drying conditions for the wet crystal, any method can be used as long as the method can retain the crystal of L-alanyl-L-glutamine dehydrate, and, for example, vacuum drying, ventilation drying, fluidized bed drying, or the like can be applied.

As a temperature for drying the wet crystal, because of the crystal of L-alanyl-L-glutamine dihydrate is transformed to the crystal of L-alanyl-L-glutamine nonhydrate when the wet crystal is dried at 40° C. or higher, it is dried generally at 0 to 35° C., and more preferably at 10 to 30° C. in the present step.

5.3 Method for Producing Crystal of L-Alanyl-L-Glutamine Nonhydrate of the Present Invention-1

The crystal of L-alanyl-L-glutamine nonhydrate of the present invention can be obtained by drying the crystal of L-alanyl-L-glutamine n-ethanolate that is collected by the step (1b) above in 5.1.2.

Specifically, for example, the crystal of L-alanyl-L-glutamine n-ethanolate of the present invention obtained by 5.1.2 above is dried under ventilation generally for 12 to 36 hours, preferably for 16 to 32 hours, and most preferably for 20 to 28 hours by using air at normal pressure and temperature which is generally 10 to 40° C., and preferably 15 to 35° C., and then the crystal of L-alanyl-L-glutamine nonhydrate of the present invention can be obtained.

As the ventilation drying, for example, a method, in which the wet crystal can be placed on a nutsche for suction or put in a device such as a flow coater, and exposed to flowing air at normal temperature and pressure, can be exemplified. Humidity and temperature of the flowing air used at this time can be adjusted in advance. As the humidity of the flowing air, generally 30% or higher, preferably 40% or higher, and more preferably 50% or higher can be exemplified.

In addition, the residual ethanol, contained in the crystal obtained by the above method, can be measured by the method in which the gas chromatograph of 3 above is used. As the residual ethanol contained in the crystal of L-alanyl-L-glutamine nonhydrate if the present invention, generally 1.0 wt % or less, preferably 0.1 wt % or less, and most preferably 0.01 wt % or less can be exemplified.

5.4 Method for Producing Crystal of L-Alanyl-L-Glutamine Nonhydrate of the Present Invention-2

The crystal of L-alanyl-L-glutamine nonhydrate of the present invention can be obtained by drying the crystal of L-alanyl-L-glutamine dihydrate that is collected by the step (2b) above in 5.2.2.

Specifically, for example, the crystal of L-alanyl-L-glutamine dihydrate of the present invention obtained by the 5.2.2 above are dried, by vacuum drying, ventilation drying or the like, generally at 40° C. or higher, preferably at 60° C. or higher, and most preferably at 95° C. or higher, and then the crystal of L-alanyl-L-glutamine nonhydrate of the present invention can be obtained. As the upper limit of the drying temperature, generally 200° C. or lower, and preferably 100° C. or lower can be exemplified.

As drying time, generally 1 to 36 hours, preferably 2 to 24 hours, and most preferably 3 to 12 hours can be exemplified.

EXAMPLE

Although examples are shown below, the present invention is not limited to the following examples.

[Example 1] Acquisition of Crystal of L-Alanyl-L-Glutamine n-Ethanolate of the Present Invention-1

200 g of crystals of L-alanyl-L-glutamine nonhydrate, which were obtained according to the method described in Japanese Patent No. 4931801, were suspended in 300 mL of 50% aqueous ethanol solution, and were left to stand at 25° C. overnight. Then, the crystals were collected by filtration and washed with a 60% aqueous ethanol solution to obtain wet crystals. The obtained wet crystals were dried under reduced pressure at 25° C. for 6 hours to obtain crystals of L-alanyl-L-glutamine (179.0 g).

The ethanol content of the crystal was 13.6 wt % as measured by using gas chromatograph. In addition, according to results of water content measurement by the thermal analysis, it was found that the crystal did not have water molecules. Accordingly, it was found that the crystal was a crystal of L-alanyl-L-glutamine n-ethanolate (0.74 ethanolate crystal).

Subsequently, the obtained crystal of L-alanyl-L-glutamine n-ethanolate was subjected to a single crystal structure analysis. The single crystal structure analysis was performed by using a curved imaging plate single crystal automatic X-ray structural analyzer R-AXIS RAPID-F (manufactured by Rigaku Corporation), according to the instruction manual. Diffraction measurement was performed by using CuK$\alpha$ rays so as to determine an initial structure according to the direct method, and then structural refinement was performed by the least squares method to obtain a final structure. As a result, it was confirmed that the crystal was surely an ethanolate crystal having no water molecules in the molecule.

Further, simulation of powder X-ray crystal diffraction patterns of the crystal of L-alanyl-L-glutamine n-ethanolate was performed based on obtained analysis results. In the simulation, the crystal structure determined by the single crystal X-ray analysis was read by Mercury and input thereto, so as to perform calculation. The calculation conditions are as follows.

X-ray wavelength: 1.54056 Å (corresponding to Cu K$\alpha$i ray)

Range of 2θ angles: 5 to 60°

Shape of peak: Pseudo-Voigt function

Full Width at Half Maximum (FWHM) of peak: 0.1°

The results of the simulation are shown in Table 1.

TABLE 1

Results of simulation of powder X-Ray crystal diffraction patterns of crystal of L-alanyl-L-glutamine n-ethanolate

| 2θ | Relative intensity |
|---|---|
| 7.6 | 100 |
| 10.7 | 60 |
| 18.4 | 40 |
| 20.7 | 5 |
| 21.4 | 31 |
| 22.1 | 21 |
| 22.6 | 5 |
| 23.3 | 30 |
| 24.4 | 27 |
| 24.7 | 6 |
| 28.0 | 6 |
| 32.3 | 11 |
| 34.9 | 5 |
| 38.3 | 5 |

In addition, results of powder X-ray diffraction of the crystal are shown in Table 2. In the table, "2θ" represents a diffraction angle (2θ°), and "relative intensity" represents a relative intensity ratio.

TABLE 2

| 2θ | Relative intensity |
|---|---|
| 7.6 | 10 |
| 10.7 | 100 |
| 18.3 | 7 |
| 20.7 | 13 |
| 21.4 | 61 |
| 22.1 | 21 |
| 22.5 | 6 |
| 23.3 | 9 |
| 24.4 | 7 |
| 24.7 | 5 |
| 27.9 | 5 |
| 32.3 | 25 |
| 34.8 | 7 |

According to the results of the powder X-ray diffraction, the obtained crystal had peaks at the diffraction angles expected based on the above simulation results (Tables 1 and 2), and thus the simulation result was confirmed to be appropriate. Therefore, it was found that the powder X-ray crystal diffraction pattern, simulated based on the crystal structure determined by the single crystal X-ray analysis, matched with the results of the actual powder X-ray diffraction.

[Example 2] Acquisition of Crystal of L-Alanyl-L-Glutamine n-Ethanolate of the Present Invention-2

The wet crystals of the L-alanyl-L-glutamine n-ethanolate obtained in Example 1 were dried under reduced pressure at each temperature of 40° C., 60° C., and 95° C., so as to obtain the crystals of L-alanyl-L-glutamine. Results of the powder X-ray diffraction of the crystal of L-alanyl-L-glutamine, which is obtained by drying under reduced pressure at 95° C. for 6 hours, are shown in Table 3. In the table, "2θ" represents a diffraction angle (2θ°), and "relative intensity" represents a relative intensity ratio.

TABLE 3

| 2θ | Relative intensity |
|---|---|
| 7.6 | 11 |
| 10.7 | 68 |
| 18.5 | 15 |
| 20.7 | 65 |
| 21.4 | 52 |
| 22.1 | 21 |
| 23.3 | 42 |
| 24.7 | 18 |
| 27.9 | 22 |
| 32.3 | 18 |
| 34.8 | 28 |

According to the results of the powder X-ray diffraction, the obtained crystal had peaks at the diffraction angles expected based on the simulation results in Example 1 (Tables 1 and 3). In addition, the ethanol content of the crystal was 7.33 wt % as measured by using gas chromatograph, and it was found that the crystal did not have water molecules according to results of water content measurement by the thermal analysis. Accordingly, it was found that the crystal was a crystal of L-alanyl-L-glutamine n-ethanolate (0.37 ethanolate crystal).

In addition, as shown in Table 6 below, according to results of measuring the ethanol content and the water content of the crystals that are dried under reduced pressure at 40° C. and 60° C., none of the crystals had water molecules and both of these contained ethanol. Accordingly, it was found that these crystals are also crystals of L-alanyl-L-glutamine n-ethanolate.

[Example 3] Acquisition of Crystal of L-Alanyl-L-Glutamine n-Ethanolate of the Present Invention-3

300 g of crystals of L-alanyl-L-glutamine nonhydrate, which were obtained according to the method described in Japanese Patent No. 4931801, were dissolved in water to prepare a L-alanyl-L-glutamine-containing aqueous solution (600 mL, L-alanyl-L-glutamine concentration: 487.5 g/L).

The aqueous solution was maintained at a temperature of 40° C., and 1200 mL of ethanol was added thereto over 12 hours, so as to precipitate crystals. Inoculation of seed crystals was not required for crystal generation. The obtained crystal slurry was cooled to 10° C. and was aged for 2 hours, and the crystals were collected by filtration and washed with a 60% aqueous ethanol solution, so as to obtain wet crystals. The wet crystals were dried under reduced pressure at 40° C. to obtain crystals of L-alanyl-L-glutamine (308.3 g).

The results of the powder X-ray diffraction of the crystal are shown in Table 4. In the table, "2θ" represents a diffraction angle (2θ°), and "relative intensity" represents a relative intensity ratio.

TABLE 4

| 2θ | Relative intensity |
|---|---|
| 10.6 | 8 |
| 18.4 | 16 |
| 20.7 | 84 |
| 21.4 | 30 |
| 22.5 | 18 |
| 23.3 | 19 |
| 24.7 | 14 |
| 27.9 | 13 |

TABLE 4-continued

| 2θ | Relative intensity |
|---|---|
| 32.4 | 6 |
| 34.8 | 30 |

According to the results of the powder X-ray diffraction, the obtained crystal had peaks at the diffraction angles expected based on the simulation results of Example 1 (Tables 1 and 4). In addition, the ethanol content of the crystal was 12.2 wt % as measured by using gas chromatograph, and it was found that the crystal did not have water molecules according to results of water content measurement by the thermal analysis. Accordingly, it was found that the crystal is a crystal of L-alanyl-L-glutamine n-ethanolate (0.66 ethanolate crystal).

[Example 4] Acquisition of Crystal of L-Alanyl-L-Glutamine n-Ethanolate of the Present Invention-4

The wet crystals of L-alanyl-L-glutamine ethanolate obtained in Example 3 were dried under reduced pressure at each temperature of 25° C., 60° C., and 95° C., so as to obtain the crystals of L-alanyl-L-glutamine.

As shown in Table 6 below, according to the results of measuring the ethanol content and the water content of the obtained crystals, none of the crystals had water molecules and all of them contained ethanol, so that it was found that these crystals are also crystals of L-alanyl-L-glutamine n-ethanolate.

About the crystal of the known nonhydrate and the ethanolate crystals obtained in Examples 1, 2 and 4, the results, which measured in terms of the loose specific volume, the dense specific volume, the angle of repose and the angle of rupture of them, are shown in Table 5.

TABLE 5

Measurement results of loose specific volume, dense specific volume, angle of repose and angle of rupture of the known nonhydrate crystal and the ethanolate crystals obtained in Examples 1, 2 and 4

| Crystal | | Loose specific volume (mL/g) | Dense specific volume (mL/g) | Angle of repose (°) | Angle of rupture (°) |
|---|---|---|---|---|---|
| Patent No. 4931801 (nonhydrate) | | 5.27 | 2.66 | 50.9 | 46.0 |
| Example 1 | 25° C. vacuum drying | 2.55 | 2.08 | 39.7 | 34.6 |
| Example 2 | 95° C. vacuum drying | 2.47 | 1.88 | 41.2 | 35.0 |
| Example 4 | 25° C. vacuum drying | 3.23 | 2.32 | 39.4 | 35.1 |
| Example 4 | 95° C. vacuum drying | 3.61 | 2.21 | 42.5 | 38.6 |

As shown in Table 5, as compared with the known nonhydrate crystal, the ethanolate crystals obtained in Examples 1, 2 and 4 show small values in terms of the loose specific volume, the dense specific volume, the angle of repose and the angle of rupture, and show excellent powder properties.

In addition, a summary of the results of measuring the ethanol content of the crystals obtained in Examples 1 to 4 by using gas chromatograph is shown in Table 6.

TABLE 6

Ethanol content of n-ethanolate crystals obtained in Examples 1 to 4

| | Crystal | Ethanol content (%) | n |
|---|---|---|---|
| Example 1 | 25° C. vacuum drying | 13.6 | 0.74 |
| Example 2 | 40° C. vacuum drying | 7.48 | 0.38 |
| Example 2 | 60° C. vacuum drying | 7.46 | 0.38 |
| Example 2 | 95° C. vacuum drying | 7.33 | 0.37 |
| Example 3 | 40° C. vacuum drying | 12.2 | 0.66 |
| Example 4 | 25° C. vacuum drying | 15.3 | 0.85 |
| Example 4 | 60° C. vacuum drying | 7.48 | 0.38 |
| Example 4 | 95° C. vacuum drying | 7.13 | 0.36 |

As shown in Table 6, the measured values of the ethanol contents of the crystals of L-alanyl-L-glutamine n-ethanolate obtained in Examples 1 to 4 fall within the range of 7.13 wt % to 15.3 wt %, so it was confirmed that these were crystals in which ethanol, whose molecule number was greater than 0 and equal to or smaller than 1, was coordinated with one molecule of L-alanyl-L-glutamine.

[Example 5] Acquisition of Crystal of L-Alanyl-L-Glutamine Nonhydrate of the Present Invention-1

The wet crystals of L-alanyl-L-glutamine n-ethanolate obtained in Example 1 were placed in a nutsche, and air under normal temperature and normal pressure was passed through by using a suction filter, so as to perform ventilation drying for 24 hours.

The analysis results of the powder X-ray diffraction of the crystals obtained by the method are shown in Table 7. In the table, "2θ" represents a diffraction angle (2θ°), and "relative intensity" represents a relative intensity ratio.

TABLE 7

| 2θ | Relative intensity |
|---|---|
| 6.9 | 5 |
| 11.2 | 5 |
| 11.6 | 5 |
| 13.5 | 34 |
| 13.7 | 100 |
| 18.4 | 20 |
| 18.7 | 37 |
| 19.6 | 40 |
| 20.3 | 21 |
| 20.7 | 90 |
| 21.1 | 24 |
| 21.4 | 35 |
| 21.6 | 17 |
| 22.5 | 27 |
| 23.0 | 12 |
| 23.3 | 15 |
| 24.1 | 24 |
| 24.8 | 19 |
| 25.3 | 18 |
| 25.4 | 22 |
| 26.0 | 10 |
| 27.6 | 16 |
| 29.8 | 7 |
| 30.5 | 7 |
| 32.4 | 7 |
| 33.0 | 8 |
| 34.1 | 11 |
| 34.8 | 36 |
| 35.2 | 10 |
| 35.7 | 8 |
| 36.5 | 13 |

TABLE 7-continued

| 2θ | Relative intensity |
|---|---|
| 36.8 | 11 |
| 37.4 | 9 |
| 38.6 | 6 |
| 39.7 | 6 |

The amount of ethanol contained in the crystal was 0.008% as measured by using gas chromatograph, in addition, it was found that the crystal did not have water molecules according to results of measuring the water content of the crystal by the thermal analysis. Accordingly, it was found that the crystal was a crystal of L-alanyl-L-glutamine nonhydrate.

About the known crystal obtained by the method described in Japanese Patent No. 4931801 and the crystal of L-alanyl-L-glutamine nonhydrate of the present invention obtained above, the results, which measured in terms of the loose specific volume, the dense specific volume, the angle of repose and the angle of rupture of them, are shown in Table 8.

TABLE 8

Measurement results of loose specific volume, dense specific volume, angle of repose and angle of rupture of the known nonhydrate crystal and the nonhydrate crystal of the present invention obtained in Example 5

| Crystal | Loose specific volume (mL/g) | Dense specific volume (mL/g) | Angle of repose (°) | Angle of rupture (°) |
|---|---|---|---|---|
| Patent No. 4931801 (nonhydrate) | 5.27 | 2.66 | 50.9 | 46.0 |
| Example 5 | 2.60 | 2.28 | 40.2 | 34.7 |

As shown in Table 8, the crystal of L-alanyl-L-glutamine nonhydrate of the present invention obtained above shows small values in terms of the loose specific volume, the angle of repose and the angle of rupture as compared with the known nonhydrate crystal, and shows excellent powder properties.

[Example 6] Acquisition of Crystal of L-Alanyl-L-Glutamine Dihydrate of the Present Invention-1

55 g of crystals of L-alanyl-L-glutamine nonhydrate, which were obtained according to the method described in Japanese Patent No. 4931801, were dissolved in water to prepare a L-alanyl-L-glutamine-containing aqueous solution (100 mL, L-alanyl-L-glutamine concentration: 550 g/L).

The aqueous solution was cooled to 10° C., so as to precipitate crystals. Inoculation of seed crystals was not required for crystal generation at that time. The crystals were collected by filtration and dried under reduced pressure at room temperature, and then the crystal of L-glutamine-L-glutamine were obtained.

The water content of the obtained crystal was 14.9 wt % as measured by the Karl-Fischer method, which was almost equal to the theoretical value of the dihydrate (14.2 wt %), therefore, it was found that the crystal was a crystal of L-alanyl-L-glutamine dihydrate.

Subsequently, the obtained crystal of L-alanyl-L-glutamine dihydrate was subjected to a single crystal structure analysis. The single crystal structure analysis was performed in a procedure similar to that in Example 1, so as to obtain a single crystal structure. As a result, it was found that the crystal was surely a crystal of L-alanyl-L-glutamine dihydrate.

Next, simulation of a powder X-ray crystal diffraction pattern of the crystal of L-alanyl-L-glutamine dihydrate, based on the single crystal structure analysis and the analysis results, was performed by the same method as Example 1. The results are shown in Table 9.

TABLE 9

Results of simulation of powder X-ray crystal diffraction pattern of crystals of L-alanyl-L-glutamine dihydrate

| 2θ | Relative intensity |
|---|---|
| 7.9 | 82 |
| 11.6 | 74 |
| 12.8 | 25 |
| 18.5 | 32 |
| 19.4 | 88 |
| 21.6 | 100 |
| 23.3 | 24 |
| 24.0 | 82 |
| 24.7 | 43 |
| 27.3 | 20 |
| 27.9 | 47 |
| 35.3 | 16 |

[Example 7] Acquisition of Crystal of L-Alanyl-L-Glutamine Dihydrate of the Present Invention-2

810 g of crystals of L-alanyl-L-glutamine nonhydrate, which were obtained according to the method described in Japanese Patent No. 4931801, were dissolved in water to prepare a L-alanyl-L-glutamine-containing aqueous solution (1.5 L, L-alanyl-L-glutamine concentration: 540 g/L).

The aqueous solution was cooled to 10° C., so as to precipitate the crystal. Inoculation of seed crystals was not required for crystal generation at that time. The crystals were collected by filtration and dried under reduced pressure at 25° C., and then the crystal of L-glutamine-L-glutamine (268.7 g) were obtained.

The results of the powder X-ray diffraction of the crystal are shown in Table 10. In the table, "2θ" represents a diffraction angle (2θ°), and "relative intensity" represents a relative intensity ratio.

TABLE 10

| 2θ | Relative intensity |
|---|---|
| 8.0 | 45 |
| 11.6 | 100 |
| 12.8 | 34 |
| 18.3 | 8 |
| 19.4 | 7 |
| 21.6 | 11 |
| 23.3 | 37 |
| 24.0 | 100 |
| 24.7 | 31 |
| 27.9 | 48 |
| 35.3 | 27 |

According to the results of the powder X-ray diffraction, the obtained crystal had peaks at the diffraction angles expected based on the simulation results of Example 6 (Tables 9 and 10). Accordingly, it was found that the crystal was a crystal of L-alanyl-L-glutamine dihydrate.

About the known crystal obtained by the method described in Japanese Patent No. 4931801 and the crystal of L-alanyl-L-glutamine dihydrate obtained above, which measured in terms of the loose specific volume, the dense specific volume, the angle of repose and the angle of rupture of them, are shown in Table 11.

TABLE 11

Measurement results of loose specific volume, dense specific volume, angle of repose and angle of rupture of the known nonhydrate crystal and the dihydrate crystal obtained in Example 7

| Crystal | Loose specific volume (mL/g) | Dense specific volume (mL/g) | Angle of repose (°) | Angle of rupture (°) |
|---|---|---|---|---|
| Patent No. 4931801 (nonhydrate) | 5.27 | 2.66 | 50.9 | 46.0 |
| Example 7 | 3.27 | 2.73 | 43.8 | 38.8 |

As shown in Table 11, the crystal of L-alanyl-L-glutamine dihydrate obtained above shows small values in terms of the loose specific volume, the angle of repose and the angle of rupture as compared with the known nonhydrate crystal, and shows excellent powder properties.

[Example 8] Acquisition of Crystal of L-Alanyl-L-Glutamine Dihydrate of the Present Invention-2

32 g of crystals of L-alanyl-L-glutamine nonhydrate, which were obtained according to the method described in Japanese Patent No. 4931801, were dissolved in water to prepare a L-alanyl-L-glutamine-containing aqueous solution (64 mL, L-alanyl-L-glutamine concentration: 500 g/L).

The aqueous solution was cooled to 10° C., and then L-alanyl-L-glutamine dihydrate was added as a seed crystal to precipitate crystals. The solution containing the crystals was maintained at 30° C., 104 mL of acetone was added over nine hours, and then was cooled to 10° C. to perform aging. The crystals were collected by filtration and dried under reduced pressure at 25° C., and then the crystal of L-glutamine-L-glutamine (31.5 g) were obtained.

The results of the powder X-ray diffraction of the crystal are shown in Table 12. In the table, "2θ" represents a diffraction angle (2θ°), and "relative intensity" represents a relative intensity ratio.

TABLE 12

| 2θ | Relative intensity |
|---|---|
| 7.9 | 29 |
| 11.6 | 100 |
| 12.8 | 27 |
| 18.3 | 9 |
| 19.4 | 6 |
| 21.6 | 11 |
| 23.3 | 47 |
| 23.9 | 98 |
| 24.7 | 30 |
| 27.9 | 49 |
| 35.3 | 35 |

According to the results of the powder X-ray diffraction, the obtained crystal had peaks at the diffraction angles expected based on the simulation results of Example 6 (Tables 9 and 12). Accordingly, it was found that the crystal was a crystal of L-alanyl-L-glutamine dihydrate.

[Example 9] Acquisition of Crystal of L-Alanyl-L-Glutamine Dihydrate of the Present Invention-3

25 g of crystals of L-alanyl-L-glutamine nonhydrate, which were obtained according to the method described in Japanese Patent No. 4931801, were dissolved in water to prepare a L-alanyl-L-glutamine-containing aqueous solution (50 mL, L-alanyl-L-glutamine concentration: 500 g/L).

The aqueous solution was cooled to 10° C., and then L-alanyl-L-glutamine dihydrate was added as a seed crystal to precipitate crystals. The solution containing the crystals was maintained at 30° C., 75 mL of isopropyl alcohol was added over three hours, and then was maintained at 30° C. to perform aging. The crystals were collected by filtration and dried under reduced pressure at 25° C., the crystal of L-glutamine-L-glutamine (13.2 g) were obtained.

The results of the powder X-ray diffraction of the crystal are shown in Table 13. In the table, "2θ" represents a diffraction angle (2θ°), and "relative intensity" represents a relative intensity ratio.

TABLE 13

| 2θ | Relative intensity |
|---|---|
| 7.9 | 22 |
| 11.6 | 95 |
| 12.8 | 24 |
| 18.3 | 8 |
| 19.4 | 11 |
| 21.6 | 15 |
| 23.3 | 48 |
| 23.9 | 100 |
| 24.7 | 23 |
| 27.9 | 38 |
| 35.3 | 37 |

According to the results of the powder X-ray diffraction, the obtained crystal had peaks at the diffraction angles expected based on the simulation results of Example 6 (Tables 9 and 13). Accordingly, it was found that the crystal was a crystal of L-alanyl-L-glutamine dihydrate.

[Example 10] Acquisition of Crystal of L-Alanyl-L-Glutamine Nonhydrate of the Present Invention-2

The crystal of L-alanyl-L-glutamine dihydrate obtained in Example 7 was placed in a separable flask and was subjected to vacuum drying. The vacuum drying was performed for 6 hours, while was rotated in contact with a water bath which was adjusted to 40° C.

As a result of measuring the water content of the crystal by the thermal analysis, the measured value of the water content of the crystal was 1.9 wt %, so it was confirmed that the crystal was a crystal of L-alanyl-L-glutamine nonhydrate.

The analysis results of the powder X-ray diffraction of the crystal obtained by the above method are shown in Table 14. In the table, "2θ" represents a diffraction angle (2θ°), and "relative intensity" represents a relative intensity ratio.

TABLE 14

| 2θ | Relative intensity |
|---|---|
| 6.9 | 2 |
| 10.7 | 1 |

TABLE 14-continued

| 2θ | Relative intensity |
|---|---|
| 12.4 | 1 |
| 13.8 | 100 |
| 17.0 | 1 |
| 17.8 | 1 |
| 18.7 | 1 |
| 20.7 | 87 |
| 21.5 | 5 |
| 22.3 | 4 |
| 22.9 | 3 |
| 23.7 | 3 |
| 25.0 | 2 |
| 26.0 | 3 |
| 27.7 | 2 |
| 29.3 | 1 |
| 30.6 | 1 |
| 34.8 | 29 |
| 36.1 | 4 |
| 37.0 | 2 |

[Example 11] Acquisition of Crystal of L-Alanyl-L-Glutamine Nonhydrate of the Present Invention-3

The crystal of L-alanyl-L-glutamine dihydrate obtained in Example 7 was placed in a separable flask and was subjected to vacuum drying. The vacuum drying was performed for 4 hours, while was rotated in contact with a water bath which was adjusted to 60° C.

As a result of measuring the water content of the crystal by the thermal analysis, the measured value of the water content of the crystal was 1.9 wt %, so it was confirmed that the crystal was a crystal of L-alanyl-L-glutamine nonhydrate.

The analysis results of the powder X-ray diffraction of the crystal obtained by the above method are shown in Table 15. In the table, "2θ" represents a diffraction angle (2θ°), and "relative intensity" represents a relative intensity ratio.

TABLE 15

| 2θ | Relative intensity |
|---|---|
| 6.9 | 2 |
| 10.7 | 1 |
| 12.4 | 1 |
| 13.8 | 100 |
| 17.1 | 1 |
| 17.8 | 1 |
| 18.7 | 1 |
| 20.7 | 88 |
| 21.5 | 5 |
| 22.3 | 4 |
| 22.9 | 3 |
| 23.7 | 3 |
| 25.1 | 2 |
| 26.0 | 3 |
| 27.7 | 2 |
| 29.3 | 1 |
| 30.6 | 1 |
| 34.9 | 30 |
| 36.1 | 4 |
| 37.0 | 2 |

[Example 12] Acquisition of Crystal of L-Alanyl-L-Glutamine Nonhydrate of the Present Invention-4

The crystal of L-alanyl-L-glutamine dihydrate obtained in Example 7 was placed in a separable flask and was subjected to vacuum drying. The vacuum drying was performed for 3 hours, while was rotated in contact with a water bath which was adjusted to 90 to 95° C.

As a result of measuring the water content of the crystal by the thermal analysis, the measured value of the water content of the crystal was 0.3 wt %, so it was confirmed that the crystal was a crystal of L-alanyl-L-glutamine nonhydrate.

The analysis results of the powder X-ray diffraction of the crystal obtained by the above method are shown in Table 16. In the table, "2θ" represents a diffraction angle (2θ°), and "relative intensity" represents a relative intensity ratio.

TABLE 16

| 2θ | Relative intensity |
|---|---|
| 6.8 | 7 |
| 13.6 | 100 |
| 13.8 | 68 |
| 20.5 | 69 |
| 20.8 | 57 |
| 21.5 | 37 |
| 22.2 | 11 |
| 22.6 | 16 |
| 23.0 | 9 |
| 23.4 | 8 |
| 24.8 | 8 |
| 25.6 | 9 |
| 26.2 | 7 |
| 27.4 | 5 |
| 34.4 | 23 |
| 34.9 | 21 |
| 36.6 | 8 |

About the known crystal obtained by the method described in Japanese Patent No. 4931801 and the crystals of L-alanyl-L-glutamine nonhydrate of the present invention obtained in Examples 10 to 12, the results, which measured in terms of the loose specific volume, the dense specific volume, the angle of repose, the angle of rupture, and the water content in the crystals as loss on drying of the thermal analysis, are shown in Table 17.

TABLE 17

Measurement results of loose specific volume, dense specific volume, angle of repose, angle of rupture, and drying loss of the known nonhydrate crystal and the nonhydrate crystals of the present invention obtained in Examples 10 to 12

| Crystal | Loose specific volume (mL/g) | Dense specific volume (mL/g) | Angle of repose (°) | Angle of rupture (°) | Drying loss (%) |
|---|---|---|---|---|---|
| Patent No. 4931801 (nonhydrate) | 5.27 | 2.66 | 50.9 | 46.0 | 0.2 |
| Example 10 | 3.69 | 2.59 | 46.4 | 39.5 | 1.9 |
| Example 11 | 3.65 | 2.84 | 42.8 | 38.0 | 1.9 |
| Example 12 | 3.07 | 2.37 | 44.7 | 41.4 | 0.3 |

As shown in Table 17, the crystals of L-alanyl-L-glutamine nonhydrate of the present invention obtained in Examples 10 to 12 show small values in terms of the loose specific volume, the angle of repose and the angle of rupture as compared with the known nonhydrate crystal, and show excellent powder properties.

Although the present invention has been described in detail with reference to specific embodiments, it will be apparent to those skilled in the art that various modifications and variations are possible without departing from the spirit and scope of the present invention. The present application is based on Japanese Patent Application No. 2016-246116 filed on Dec. 20, 2016, the contents of which are incorporated herein by reference. In addition, all references cited herein are incorporated in their entirety.

INDUSTRIAL APPLICABILITY

The present invention provides a crystal of L-alanyl-L-glutamine useful for, for example, as a products, a raw material, an intermediate, or the like of health food, pharmaceuticals, cosmetics, or the like, and a method for producing the same.

The invention claimed is:

1. Crystalline L-alanyl-L-glutamine, wherein the loose specific volume is 5.0 mL/g or less.

2. The crystalline L-alanyl-L-glutamine according to claim 1, wherein the angle of repose is 50° or less.

3. The crystalline L-alanyl-L-glutamine according to claim 1, which is crystalline L-alanyl-L-glutamine nonhydrate.

4. The crystalline L-alanyl-L-glutamine according to claim 3, which has peaks at diffraction angles($2\theta°$) of 13.7°±0.2°, 20.7°±0.2°, and 34.9°±0.2° in powder X-ray diffraction.

5. The crystalline L-alanyl-L-glutamine according to claim 4, which further has peaks at diffraction angles($2\theta°$) of 21.5°±0.2°, and 22.3°±0.2° in powder X-ray diffraction.

6. The crystalline L-alanyl-L-glutamine according to claim 1, which is crystalline L-alanyl-L-glutamine n-ethanolate, wherein n represents any number greater than 0.

7. The crystalline L-alanyl-L-glutamine according to claim 6, which has peaks at diffraction angles($2\theta°$) of 10.7°±0.2°, 20.7°±0.2°, 21.4°±0.2°, 23.3°±0.2°, and 34.8°±0.2° in powder X-ray diffraction.

8. The crystalline L-alanyl-L-glutamine according to claim 7, which further has peaks at diffraction angles($2\theta°$) of 18.4°±0.2°, 24.7°±0.2°, 27.9°±0.2°, and 32.3°±0.2° in powder X-ray diffraction.

9. The crystalline L-alanyl-L-glutamine according to claim 1, which is crystalline L-alanyl-L-glutamine dihydrate.

10. The crystalline L-alanyl-L-glutamine according to claim 9, which has peaks at diffraction angles($2\theta°$) of 11.6°±0.2°, 23.3°±0.2°, 23.9°±0.2°, 27.9°±0.2°, and 35.3°±0.2° in powder X-ray diffraction.

11. The crystalline L-alanyl-L-glutamine according to claim 10, which further has peaks at diffraction angles($2\theta°$) of 7.9°±0.2°, 12.8°±0.2°, 18.3°±0.2°, 21.6°±0.2°, and 24.7°±0.2° in powder X-ray diffraction.

12. A method for producing the crystalline L-alanyl-L-glutamine according to claim 3, comprising the following steps (1a) to (1c), wherein n represents any number greater than 0:

(1a) the step of precipitating crystalline L-alanyl-L-glutamine n-ethanolate by adding or dropping ethanol to an aqueous solution in which L-alanyl-L-glutamine is dissolved, or the step of transforming the crystalline L-alanyl-L-glutamine nonhydrate to crystalline L-alanyl-L-glutamine n-ethanolate by suspending crystalline L-alanyl-L-glutamine nonhydrate in an aqueous ethanol solution;

(1b) the step of collecting the crystalline L-alanyl-L-glutamine n-ethanolate, which is obtained by the precipitation or the transformation, from the aqueous solution in which the L-alanyl-L-glutamine is dissolved or the aqueous ethanol solution; and (1c) the step of obtaining the crystalline L-alanyl-L-glutamine nonhydrate by ventilation drying the collected crystalline L-alanyl-L-glutamine n-ethanolate.

13. A method for producing the crystalline L-alanyl-L-glutamine according to claim 3, the method comprising the following steps (2a) to (2c):

(2a) the step of precipitating crystalline L-alanyl-L-glutamine dihydrate by cooling an aqueous solution, in which L-alanyl-L-glutamine is dissolved, to 35° C. or lower, or by adding or dropping at least one solvent selected from the group consisting of alcohols and ketones into the aqueous solution while keeping the aqueous solution, in which L-alanyl-L-glutamine is dissolved, at 35° C. or lower;

(2b) the step of collecting the precipitated crystalline L-alanyl-L-glutamine dihydrate; and (2c) the step of obtaining crystalline L-alanyl-L-glutamine nonhydrate by drying the collected crystalline L-alanyl-L-glutamine dihydrate at 40° C. or higher.

14. A method for producing crystalline L-alanyl-L-glutamine dihydrate, the method comprising the following steps (2a) and (2b):

(2a) the step of precipitating the crystalline L-alanyl-L-glutamine dihydrate by cooling an aqueous solution, in which L-alanyl-L-glutamine is dissolved, to 35° C. or lower, or by adding or dropping at least one solvent selected from the group consisting of alcohols and ketones into the aqueous solution while keeping the aqueous solution, in which L-alanyl-L-glutamine is dissolved, at 35° C. or lower; and (2b) the step of collecting the precipitated crystalline L-alanyl-L-glutamine dihydrate from the aqueous solution.

15. The production method according to claim 14, in which the alcohols are at least one alcohol selected from the group consisting of methanol, ethanol, n-propyl alcohol and isopropyl alcohol.

16. The production method according to claim 14, in which the ketones are acetone.

17. The production method according to claim 13, in which the alcohols are at least one alcohol selected from the group consisting of methanol, ethanol, n-propyl alcohol and isopropyl alcohol.

18. The production method according to claim 13, in which the ketones are acetone.

* * * * *